US010828342B2

(12) United States Patent
Ricard et al.

(10) Patent No.: US 10,828,342 B2
(45) Date of Patent: Nov. 10, 2020

(54) USE OF CRANBERRY PROANTHOCYANIDIN FOR TREATMENT OF OROPHARYNGEAL BACTERIAL COLONIZATION

(71) Applicants: INSTITUT NATIONAL DE LA SANTE ET DE LA RECHERCHE MEDICALE (INSERM), Paris (FR); UNIVERSITE PARIS DIDEROT—PARIS 7, Paris (FR); ASSISTANCE PUBLIQUE—HÔPITAUX DE PARIS, Paris (FR)

(72) Inventors: Jean-Damien Ricard, Paris (FR); Dimitri Margetis, Paris (FR)

(73) Assignees: INSTITUT NATIONAL DE LA SANTE ET DE LA RECHERCHE MEDICALE (INSERM), Paris (FR); UNIVERSITE PARIS DIDEROT—PARIS 7, Paris (FR); ASSISTANCE PUBLIQUE—HÔPITAUX DE PARIS, Paris (FR)

( * ) Notice: Subject to any disclaimer, the term of this patent is extended or adjusted under 35 U.S.C. 154(b) by 0 days.

(21) Appl. No.: 15/303,118

(22) PCT Filed: Apr. 9, 2015

(86) PCT No.: PCT/IB2015/052577
§ 371 (c)(1),
(2) Date: Oct. 10, 2016

(87) PCT Pub. No.: WO2015/155722
PCT Pub. Date: Oct. 15, 2015

(65) Prior Publication Data
US 2017/0028006 A1   Feb. 2, 2017

(30) Foreign Application Priority Data
Apr. 11, 2014   (EP) .................................... 14305539

(51) Int. Cl.
*A61K 36/45* (2006.01)
*A61K 31/352* (2006.01)

(52) U.S. Cl.
CPC ............ *A61K 36/45* (2013.01); *A61K 31/352* (2013.01); *Y02A 50/30* (2018.01)

(58) Field of Classification Search
CPC ....... A61K 31/352; A61K 36/45; A61P 11/00; A61P 31/04; Y02A 50/30; Y02A 50/473
See application file for complete search history.

(56) References Cited

U.S. PATENT DOCUMENTS

| 5,474,774 A * | 12/1995 | Walker ..................... A61K 8/97 424/732 |
| 5,646,178 A * | 7/1997 | Walker .................. A61K 31/353 424/732 |
| 6,391,330 B1 * | 5/2002 | Ross .................... A61K 9/0043 424/434 |
| 2011/0038917 A1 * | 2/2011 | Kappers ............... A61K 31/353 424/443 |
| 2011/0059193 A1 * | 3/2011 | Tournay ................. A61K 36/45 424/732 |
| 2014/0004214 A1 * | 1/2014 | Kedrowski ............ A61K 36/45 424/732 |

FOREIGN PATENT DOCUMENTS

| EP | 1153605 A1 | 11/2001 |
| KR | 20110071587 A | 6/2011 |
| WO | 2013/006458 A1 | 1/2013 |
| WO | 2013/023340 A1 | 2/2013 |

OTHER PUBLICATIONS

Struelens, BMJ, 1998, 652-654, Champs, J of Clin. Microbiology, 1993, p. 123-127.*
Duedu et al. Int J of Microbiology, 2017, p. 1-6.*
Choo, Infection and Chemotherapy, 2017, 49, 2, 158-159.*
Krueger et al. (Anal Biochem, Feb. 2013).*
Public Health England (https://www.ncbi.nlm.nih.gov/pmc/articles/PMC3107499/pdf/nihms296483.pdf, p. 1-34, 2015.*
Amaral et al. (J Bras Pneumol. 2009, 35(11):1116-1124). (Year: 2009).*
Cranberry, The Color of Health (https://www.fs.fed.us/wildflowers/ethnobotany/documents/Brochure_COH.pdf, 2000 (Year: 2000).*
Bonifait et al. (Clinical Review, J Can Dent Assoc 2010, p. 1-4) (Year: 2010).*
CDER Jul. 2005 (Year: 2005).*
NIH, https://nccih.nih.gov/health/cranberry, 2016 (Year: 2016).*
Lee et al. (eCAM 2010, 7, (2), 227-232) (Year: 2010).*
Johanson et al. (Annals of Internal Medicine, 77, 701-706, 1972) (Year: 1972).*
Botto et al. (Scandinavian J of Urology and Nephrology, 2010, 1-4) (Year: 2010).*
Dugoua et al. (Can J Clin Pharmacol vol. 15, 1, 2008, e80-86) (Year: 2008).*
Huttunen et al. (Phytotherapy Research, 25, 122-127, 2011) (Year: 2011).*
Karine Feghali et al: "Cranberry Proanthocyanidins: Natural Weapons against Periodontal Diseases", Journal of Agricultural and Food Chemistry, vol. 60, No. 23, Jun. 13, 2012, pp. 5728-5735.
Vu Dang La et al: "Cytoprotective effect of Proanthocyanidin-rich cranberry fraction against bacterial cell wall-mediated toxicity in macrophages and epithelial cells", Phytotherapy Research, vol. 23, No. 10, Oct. 1, 2009, pp. 1449-1452.

(Continued)

*Primary Examiner* — Umamaheswari Ramachandran
(74) *Attorney, Agent, or Firm* — W&C IP

(57) ABSTRACT

The present invention relates to a method for preventing Gram-negative bacterial colonization of an oropharyngeal material, the said method comprising bringing into contact a composition comprising a cranberry-derived proanthocyanidin extract on at least a part of the surface area of the said material.

11 Claims, 23 Drawing Sheets

(56) References Cited

OTHER PUBLICATIONS

Figure 1:
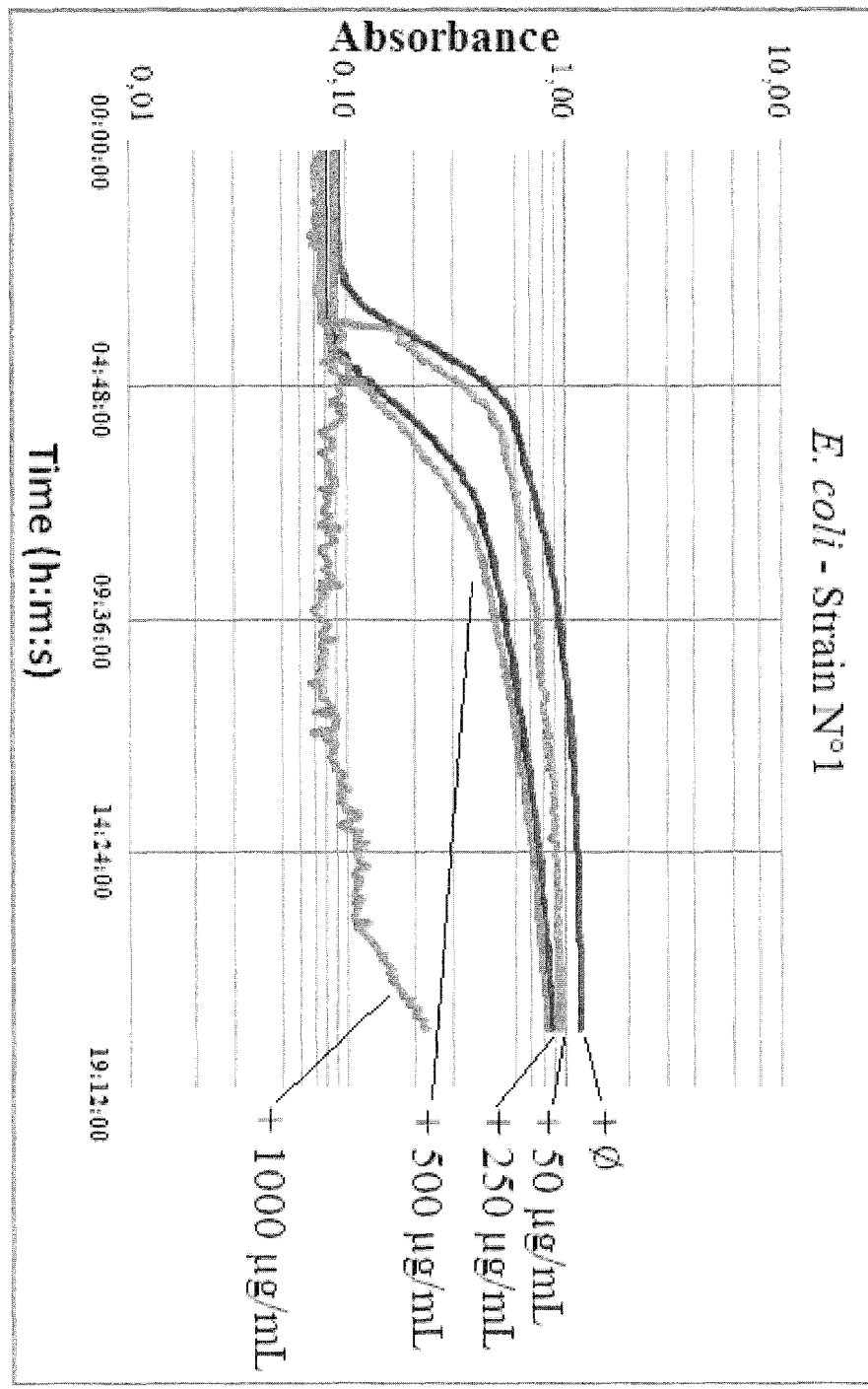
Figure 2:
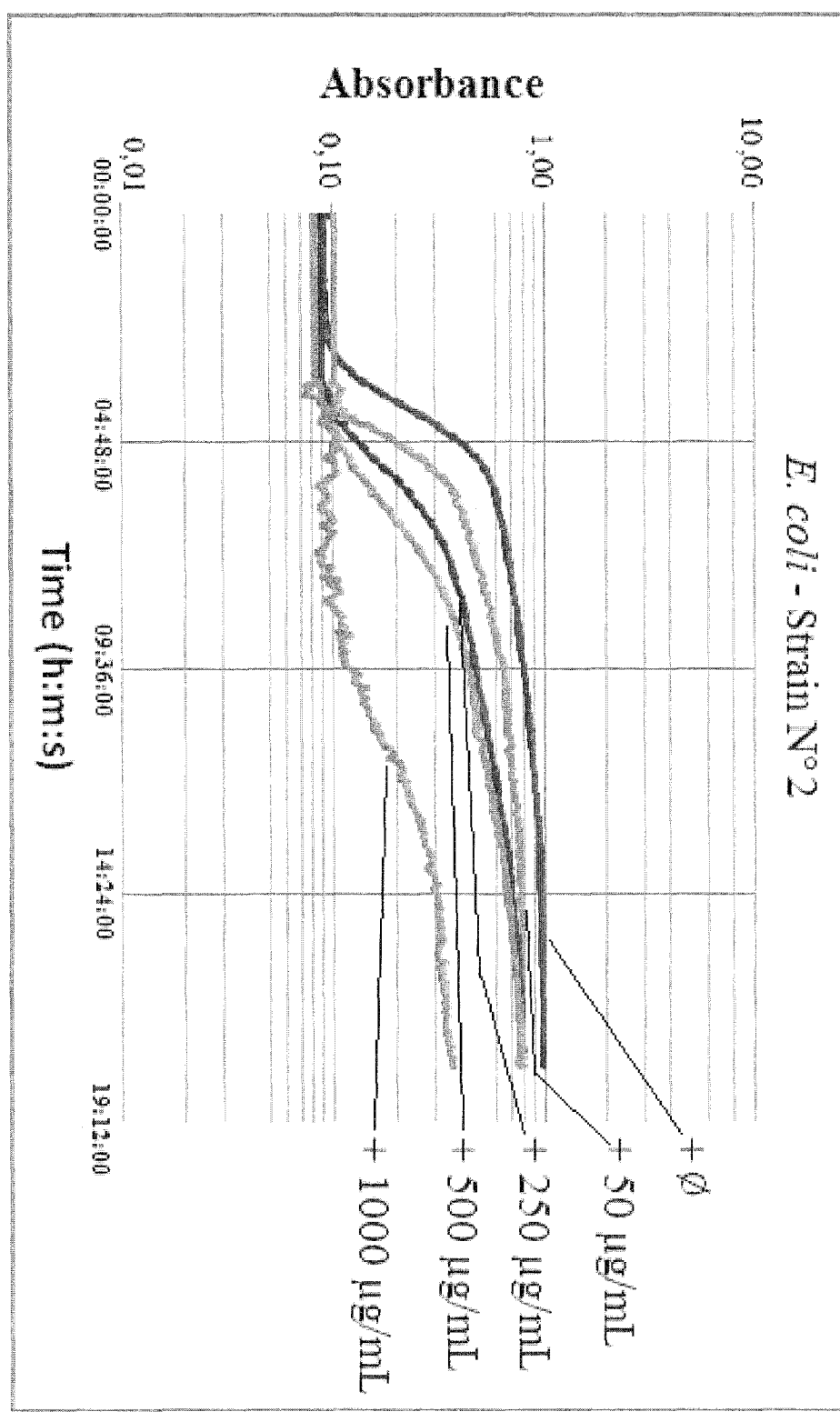
Figure 3:
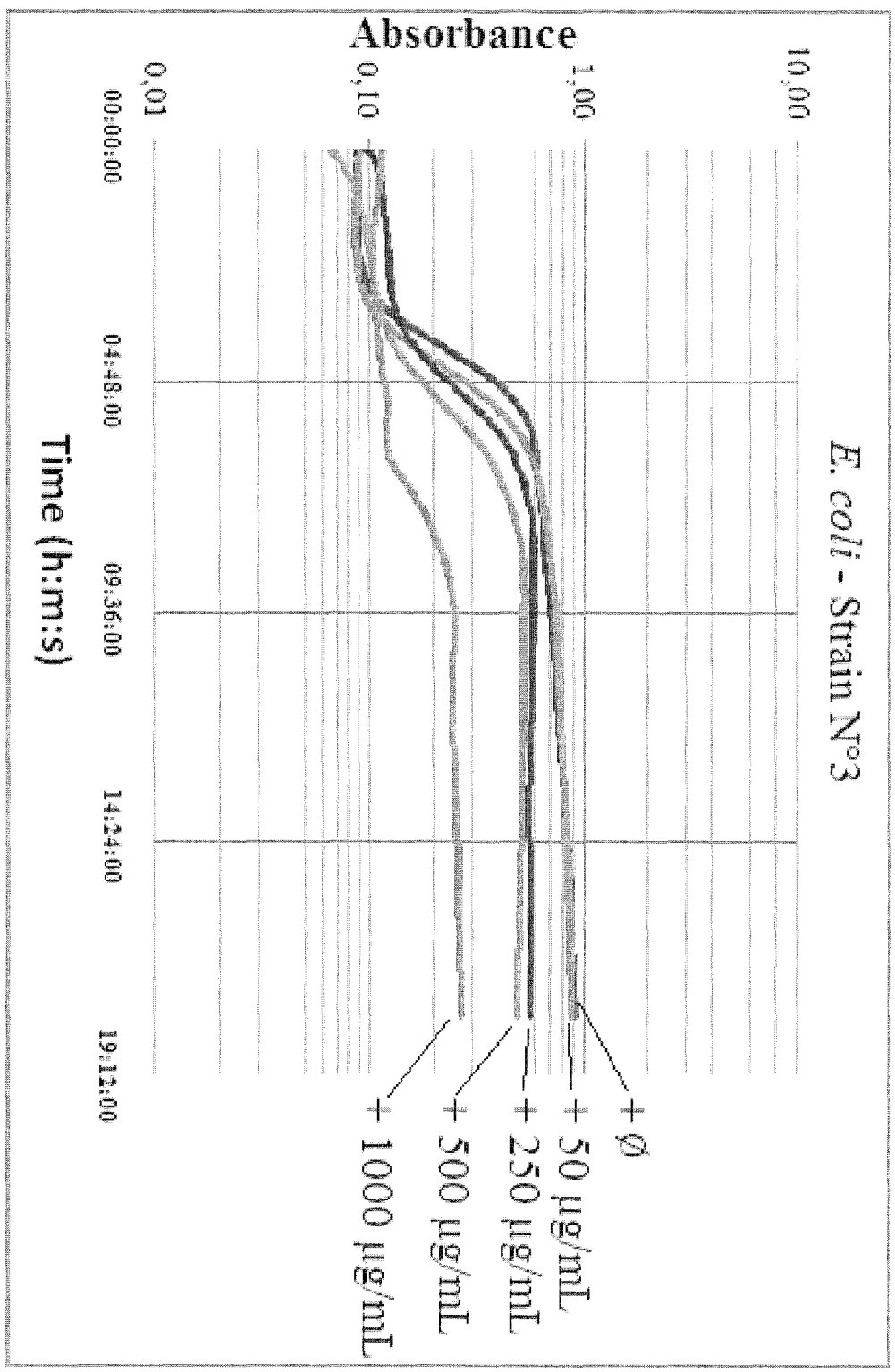
Figure 4:
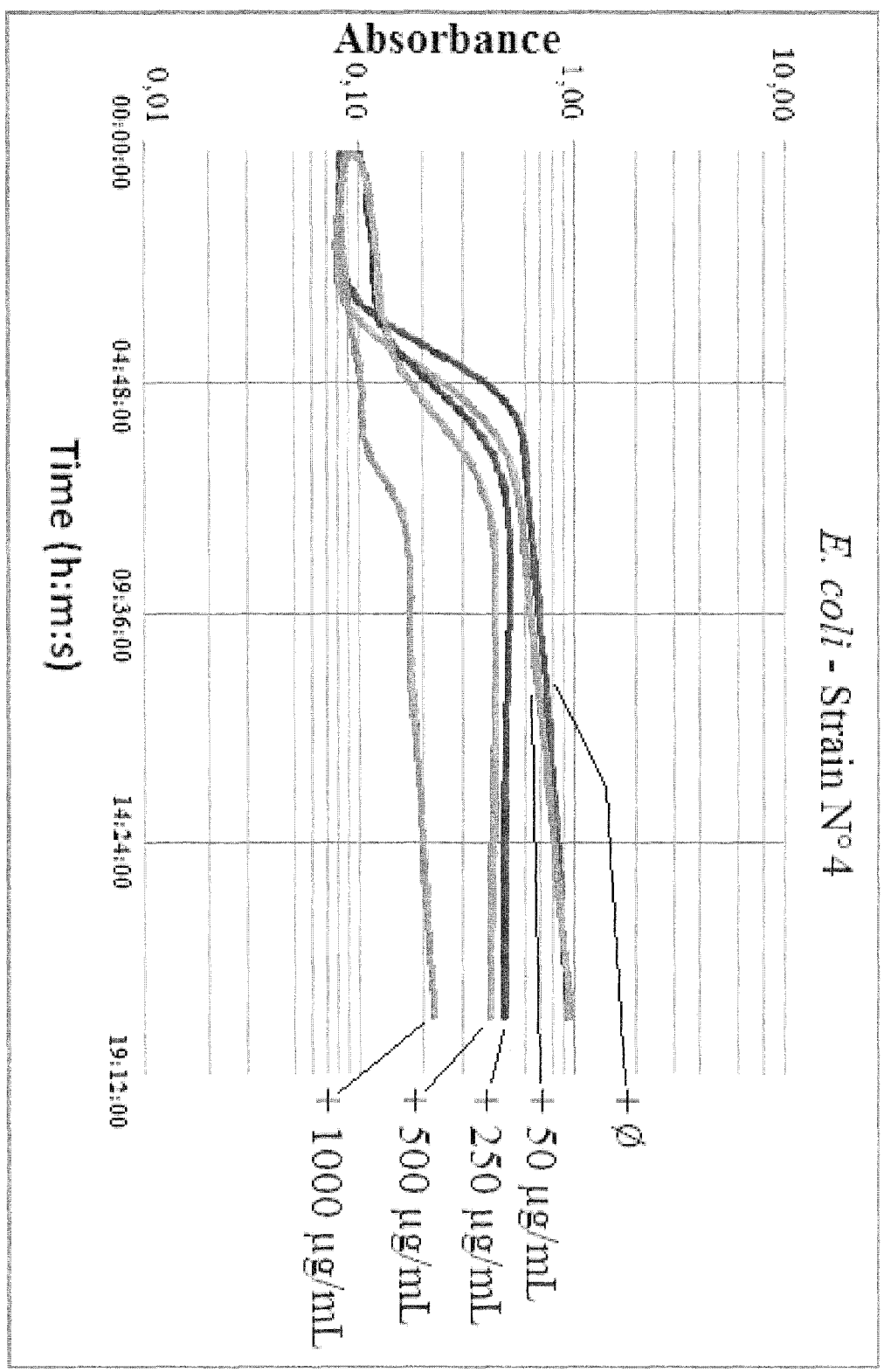
Figure 5:
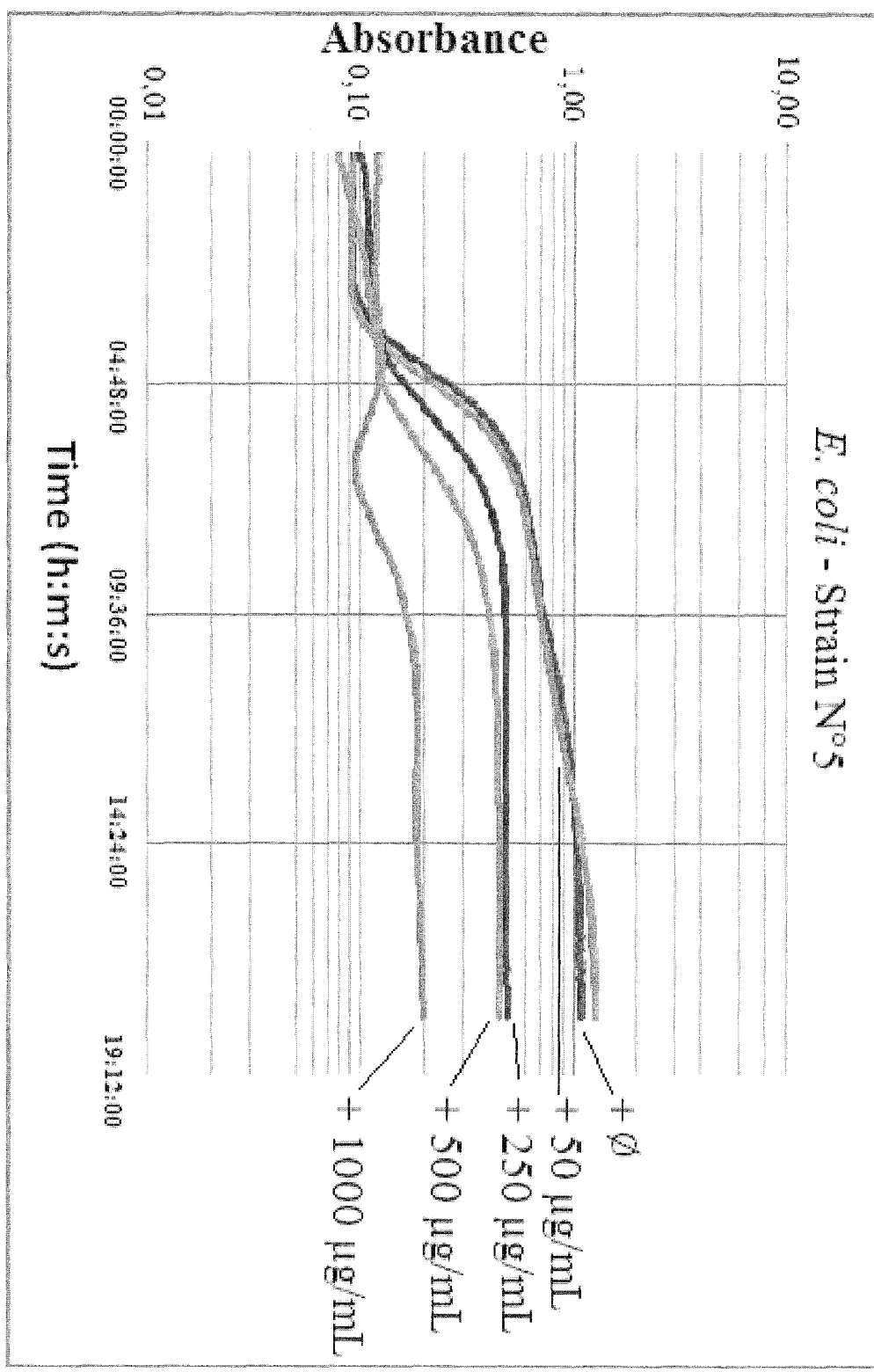
Figure 6:
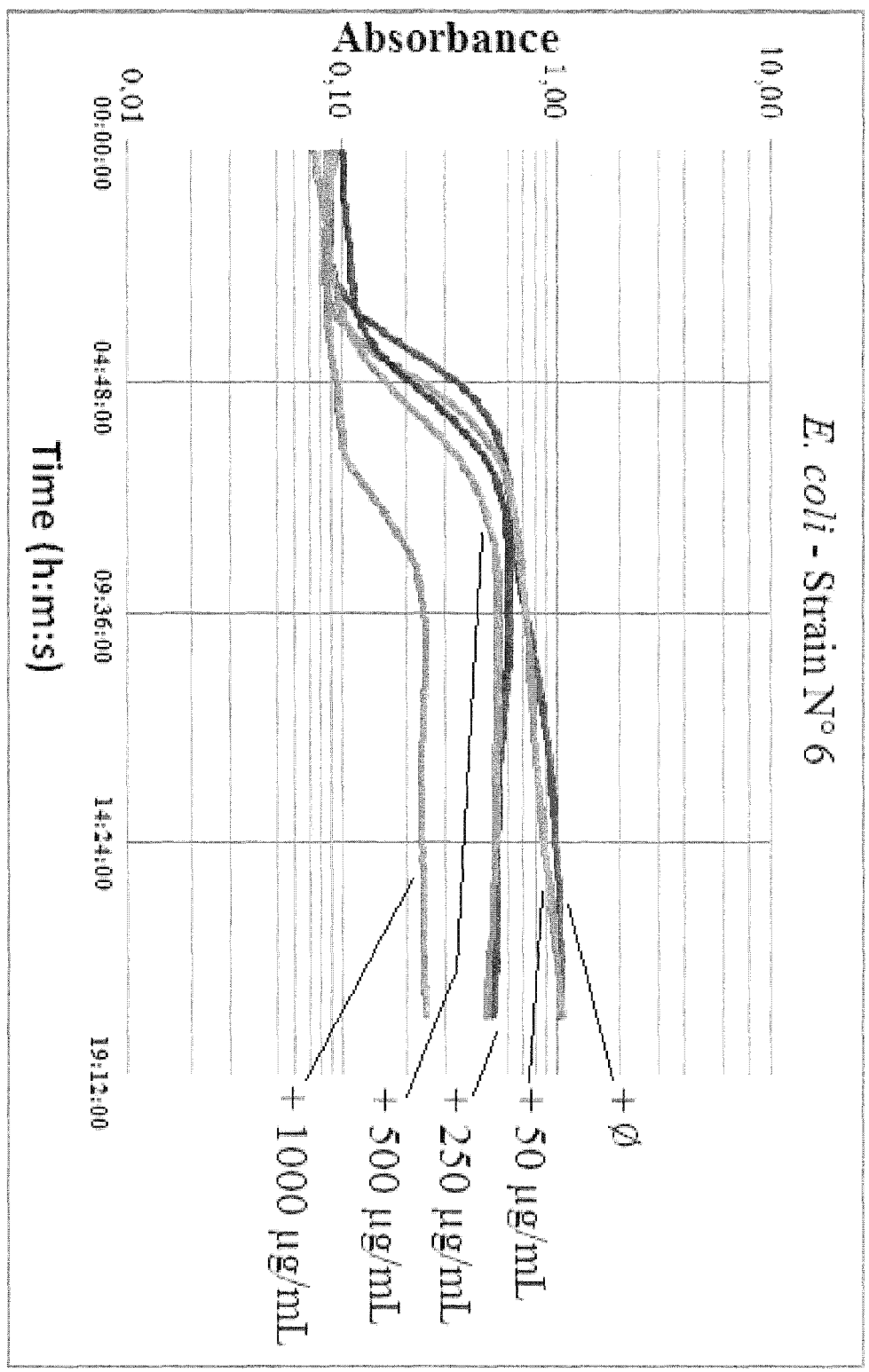
Figure 7:
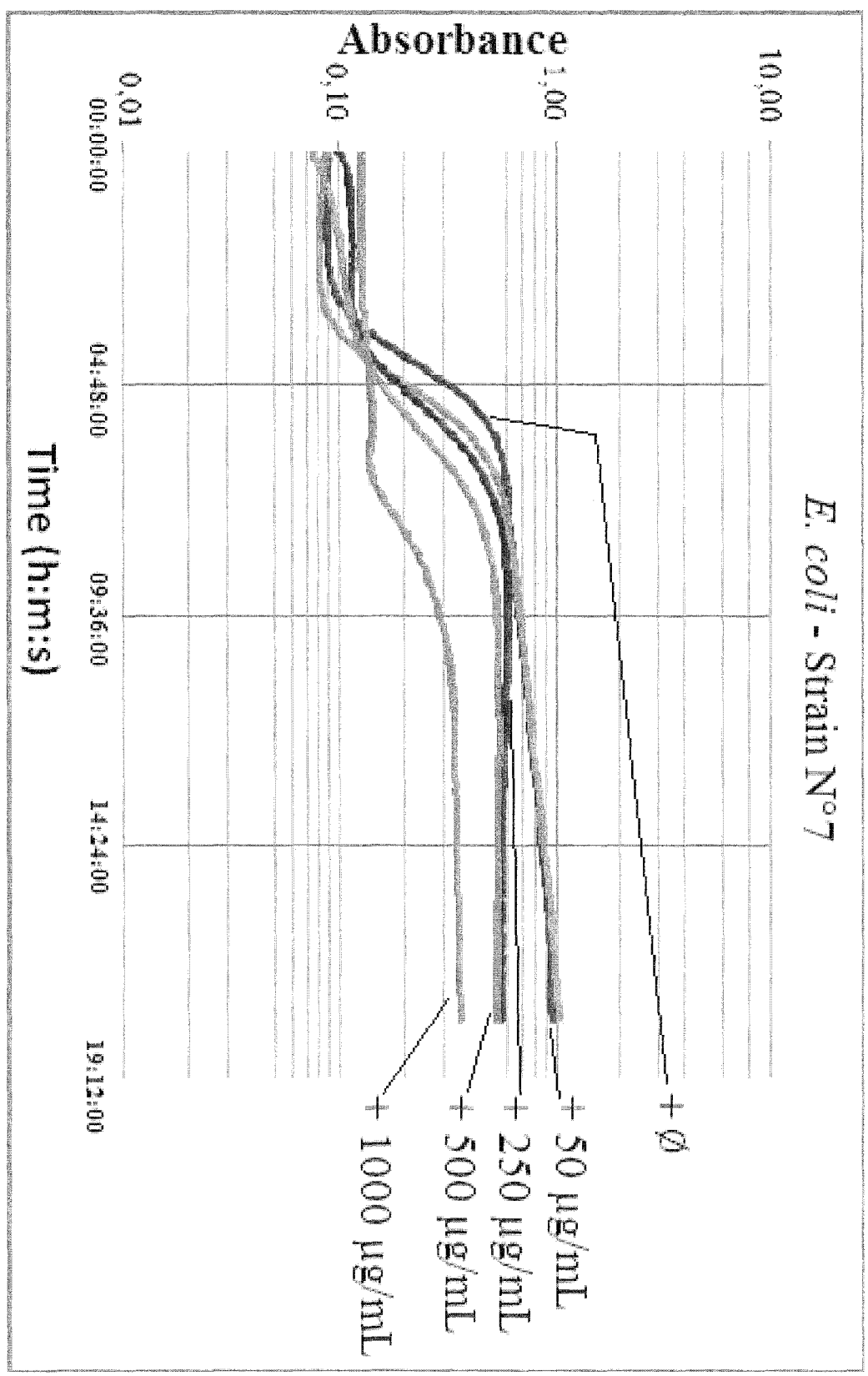
Figure 8:
Figure 9:
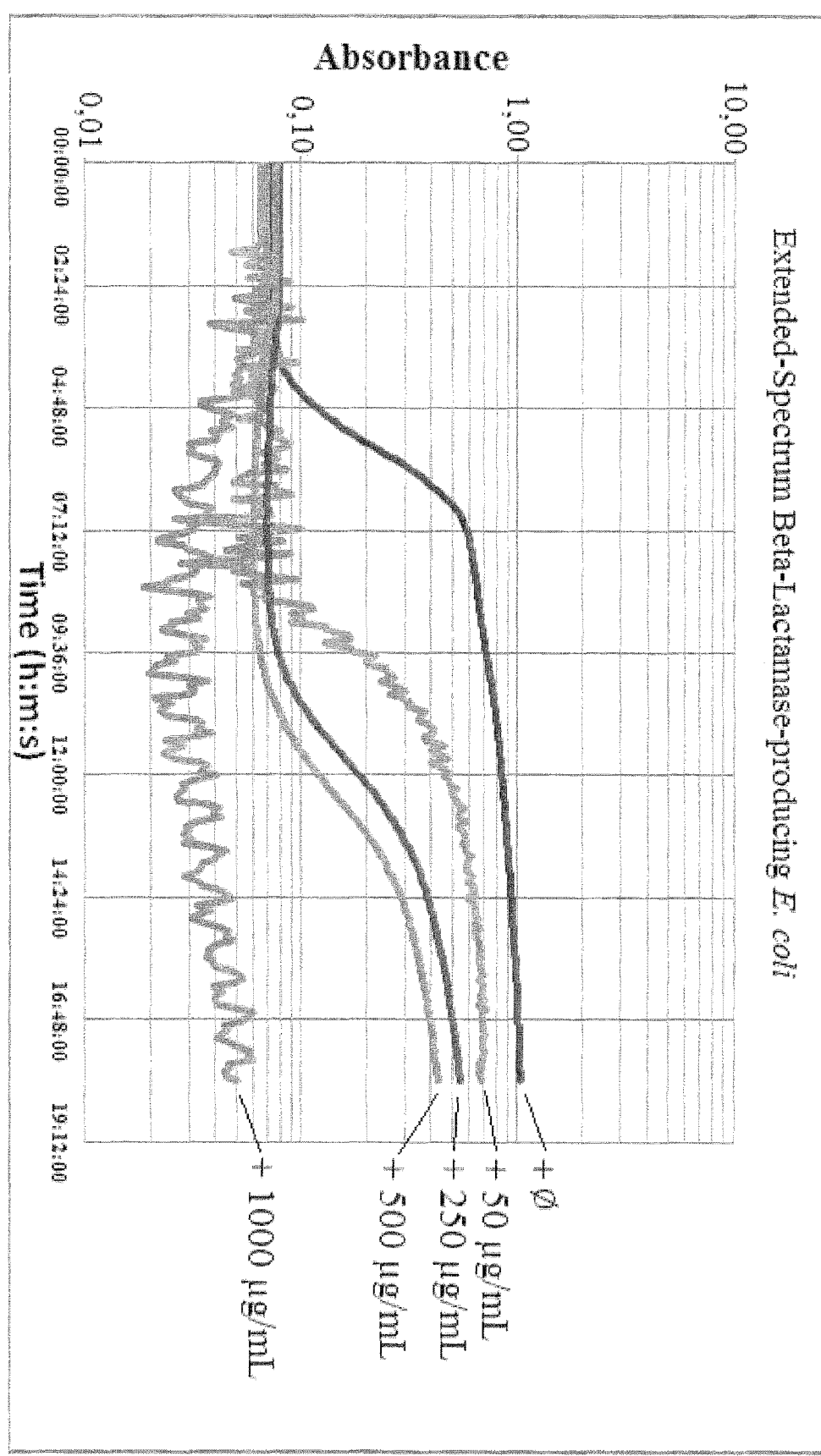
Figure 10:
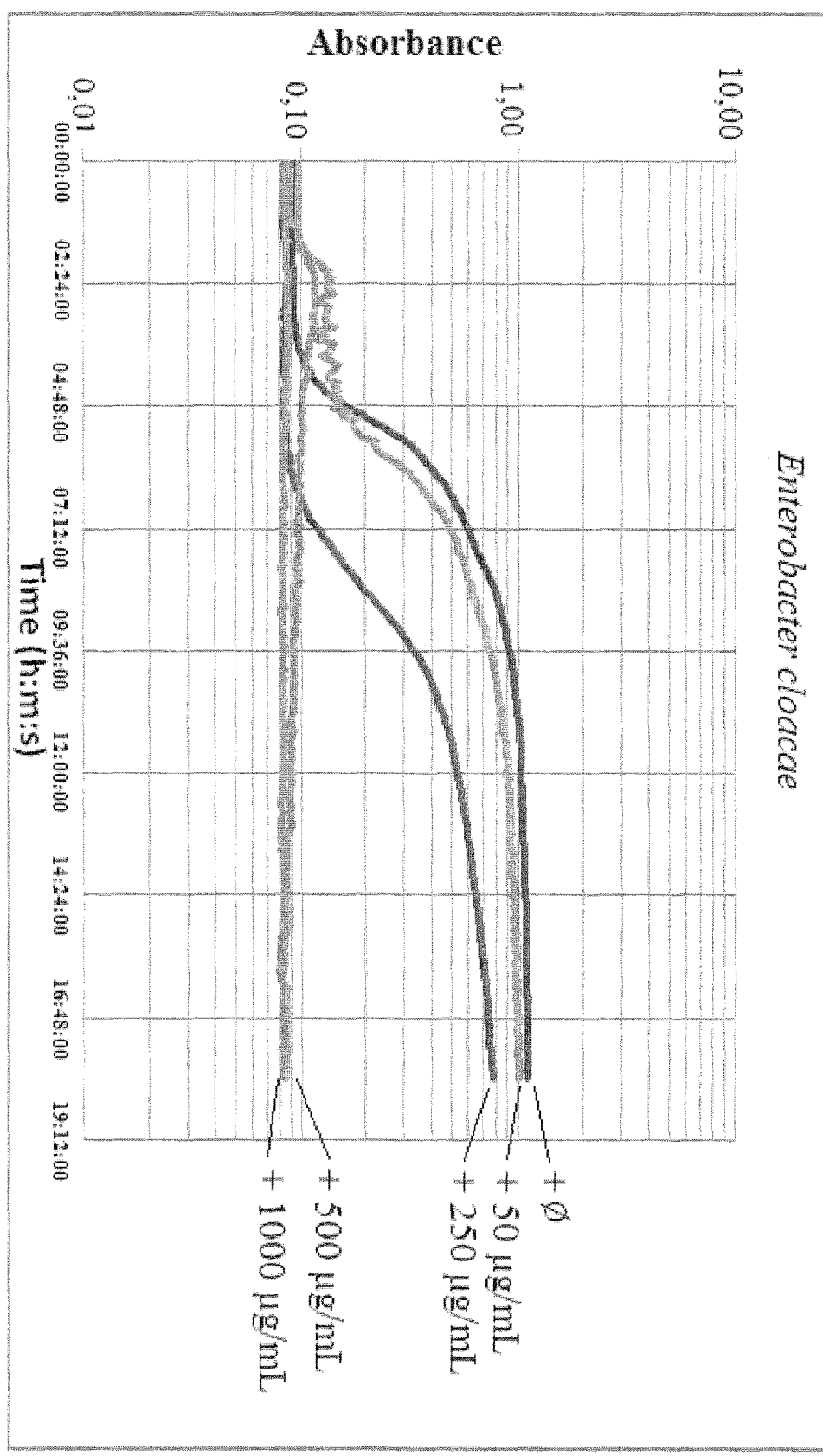
Figure 11:
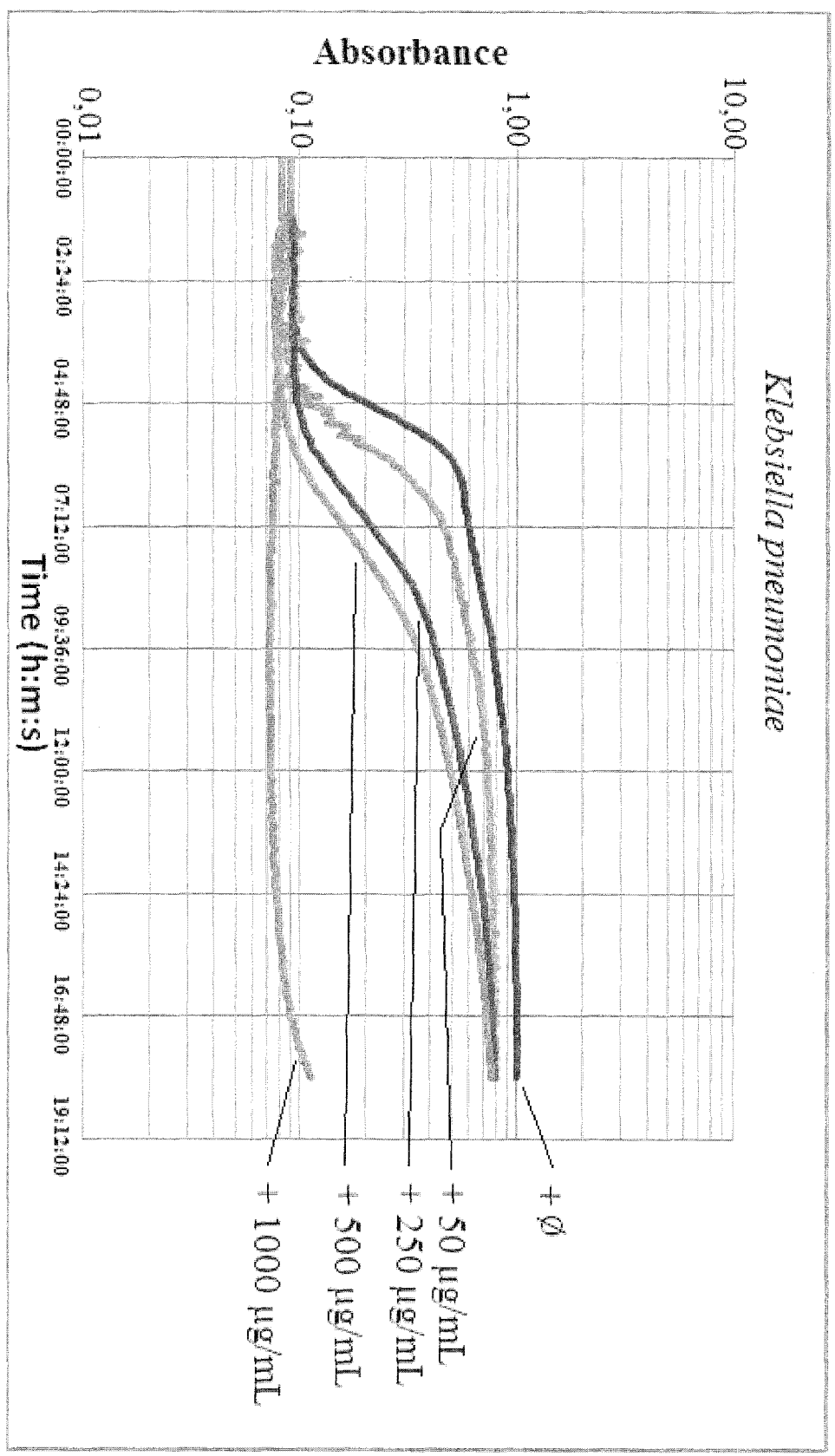
Figure 12:
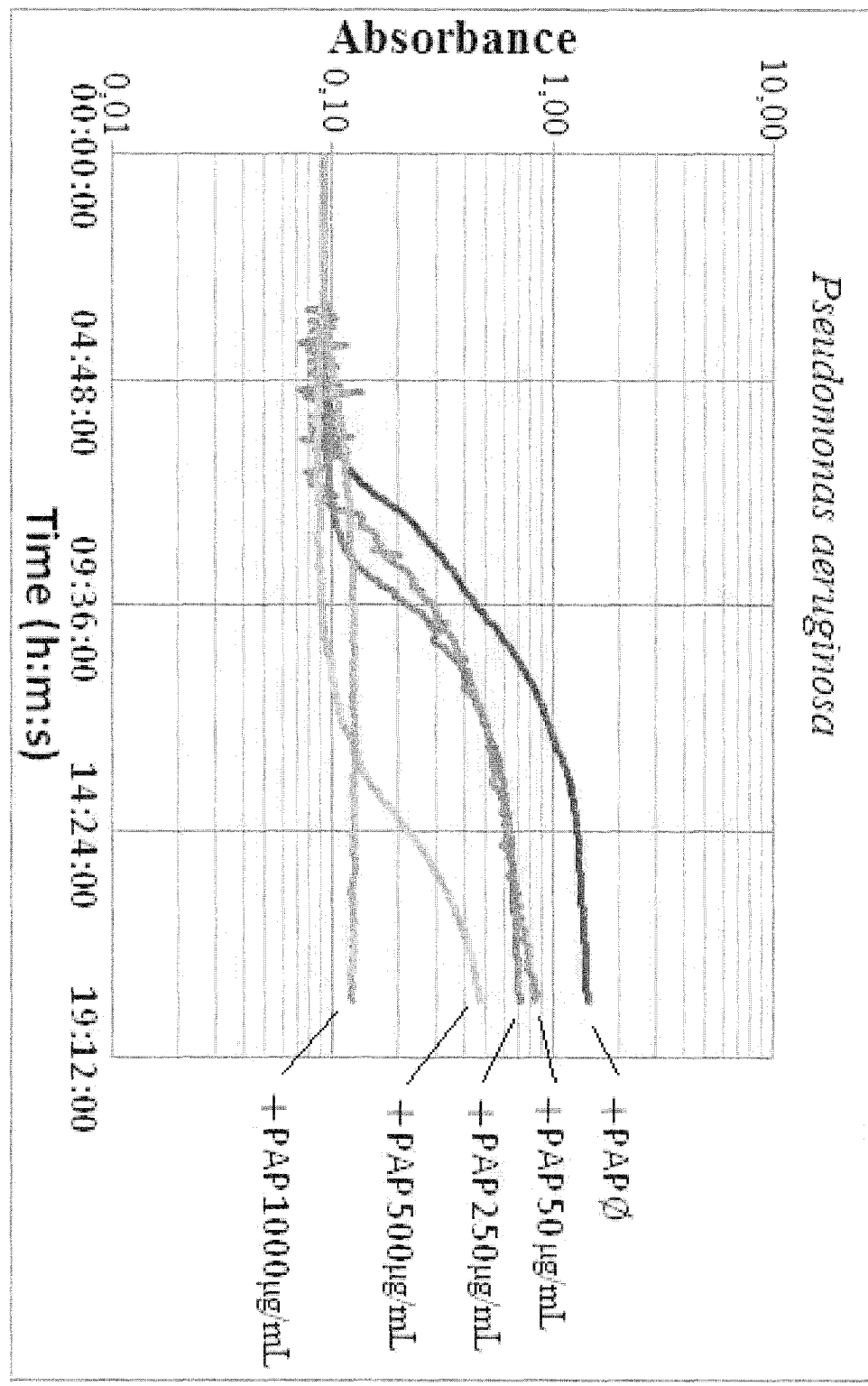
Figure 13:
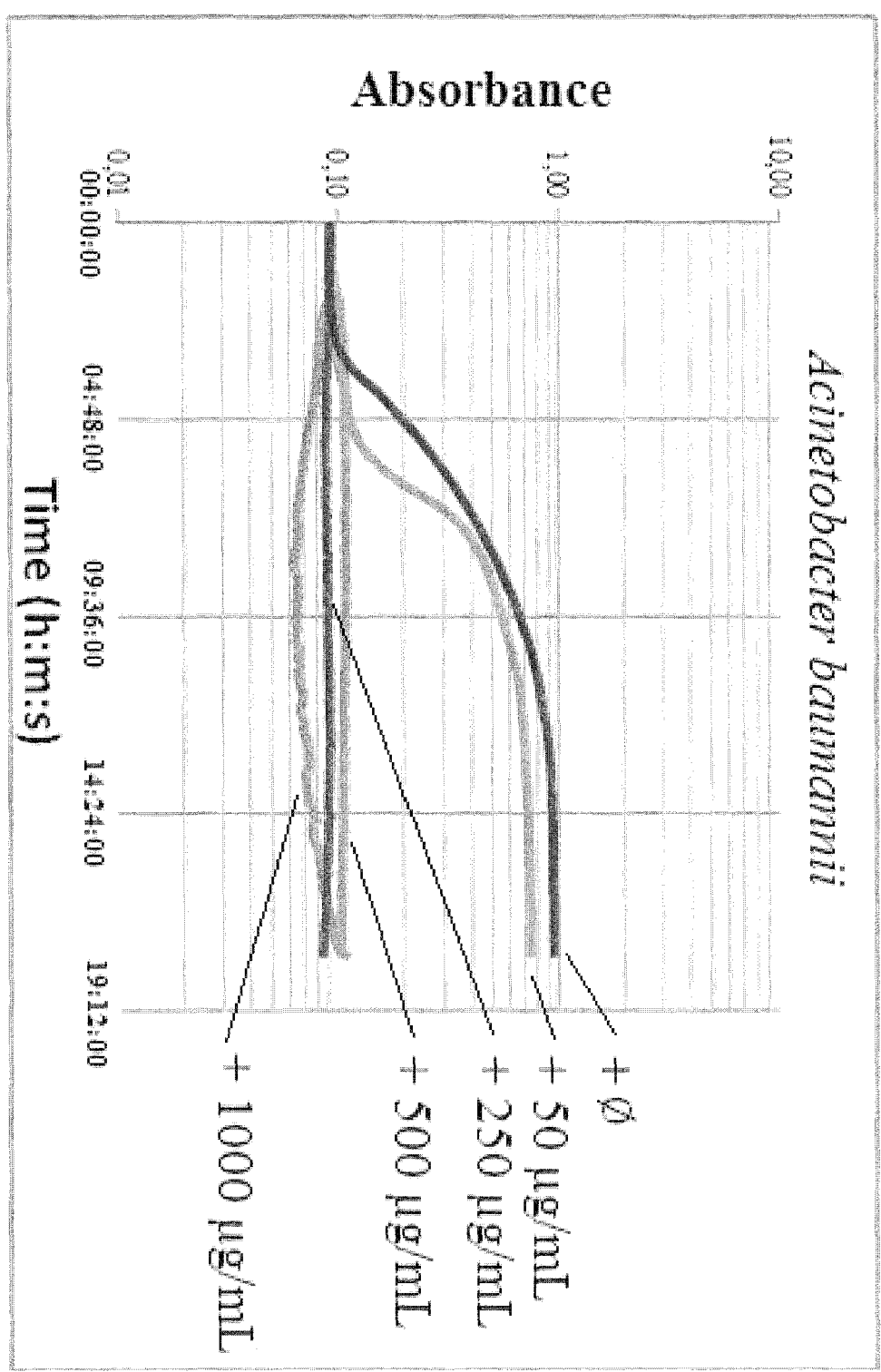
Figure 14:
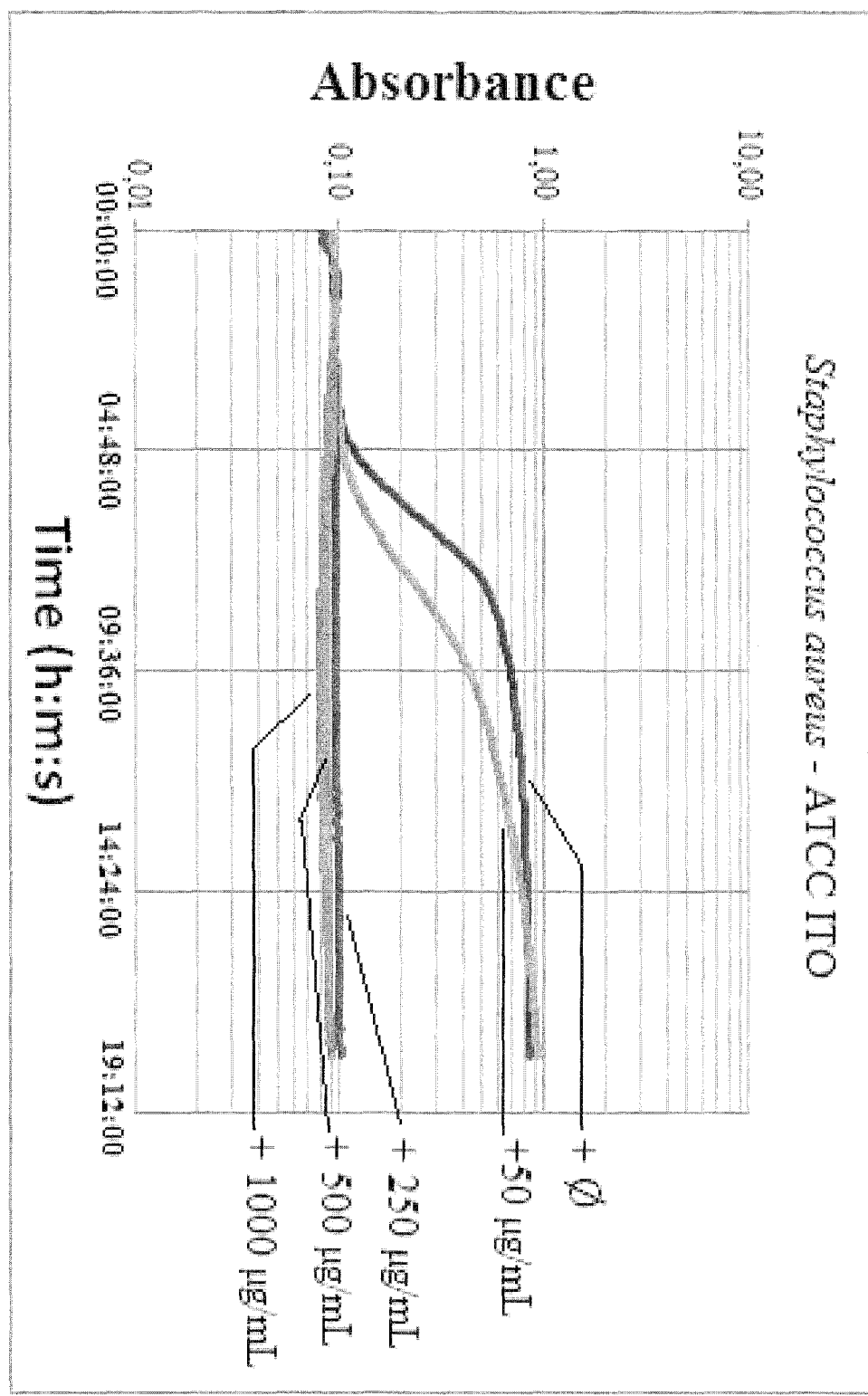
Figure 15:
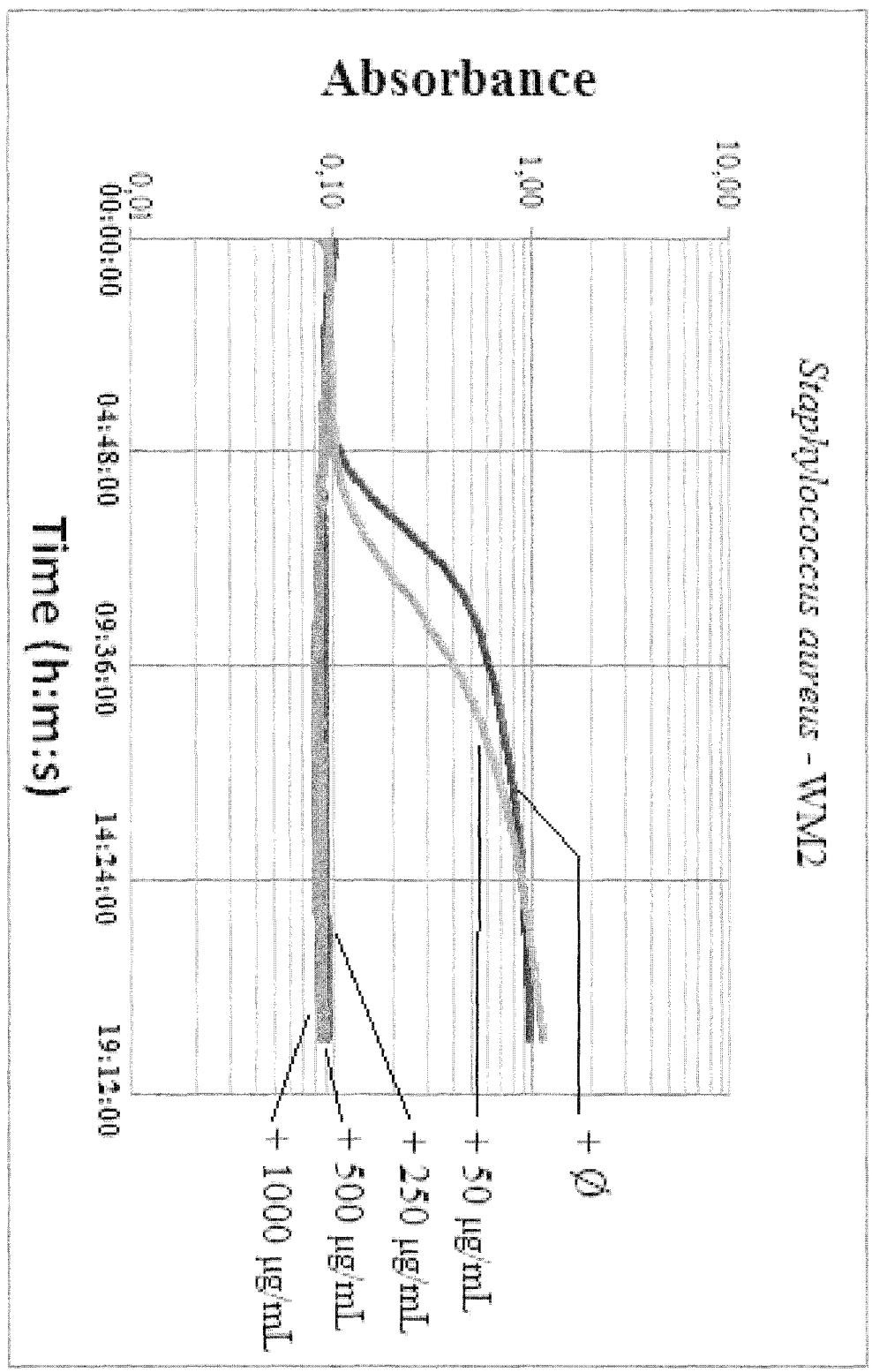
Figure 16:
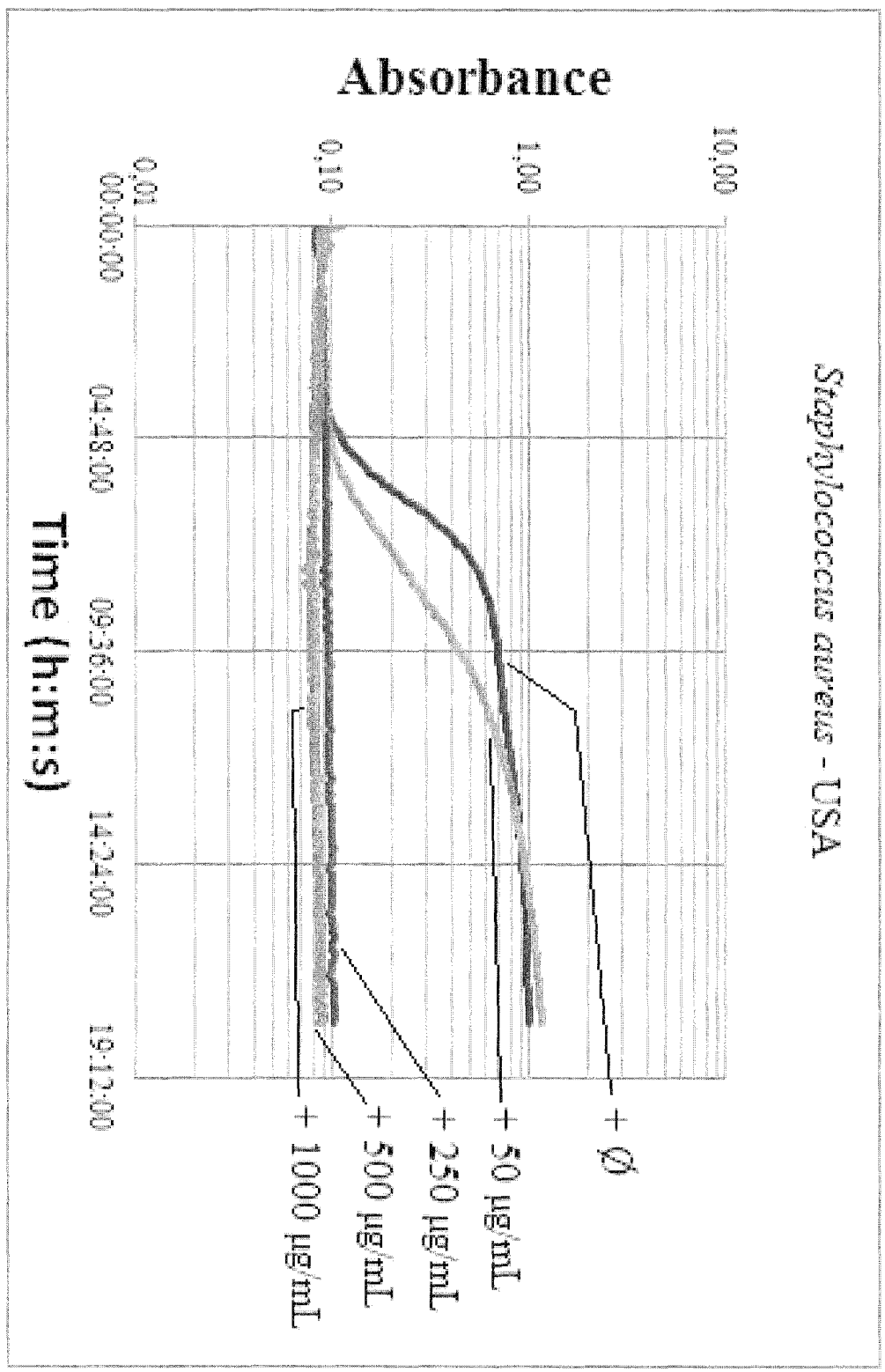

Scannapieco Frank A et al: "The relationship between periodontal diseases and respiratory diseases.", Dentistry Today, vol. 22, No. 8, Aug. 2003, pp. 79-83.
Yeap Lai et al: "The structure of cranberry proanthocyanidins which inhibit adherence of uropathogenic P-mbriated *Escherichia coli* in vitro", Phytochemistry, vol. 54 Nov. 30, 2000, pp. 173-181.
Petri Kylli et al: "Lingonberry (Vaccinium vitis-idaea) and European Cranberry (Vaccinium microcarpon) Proanthocyanidins: Isolation, Identification, and Bioactivities", Journal of Agricultural and Food Chemistry, vo. 59, No. 7, Apr. 13, 2011, pp. 3373-3384.
Database Biosis [Online] Biosciences Information Service, Philadelphia, PA, US; May 2011, O'May Che et al: "The Swarming Motility of Pseudomonas aeruginosa Is Blocked by Cranberry Proanthocyanidins and Other Tannin-Containing Materials".
Pineda Lilibeth A et al: "Effect of oral decontamination with chlorhexidine on the incidence of nosocomial pneumonia: a meta-analysis", Critical Care, Biomed Central Ltd., London, GB, vol. 10. No. 1, Feb. 20, 2006, p. R35.

\* cited by examiner

USE OF CRANBERRY PROANTHOCYANIDIN FOR TREATMENT OF OROPHARYNGEAL BACTERIAL COLONIZATION

FIELD OF THE INVENTION

The present invention relates to antibacterial substances for use in the medical field, especially for the purpose of preventing nosocomial infections, in particular nosocomial pneumonia.

More particularly, the present invention relates to substances providing a bacteriostatic effect.

BACKGROUND OF THE INVENTION

The United States Centers for Disease Control and Prevention (CDC) has estimated that about 2 million patients suffer from Hospital-Acquired infections (HAIs) every year and nearly 100,000 of them die.

HAIs result in up to $4.5 billion in additional healthcare expenses annually in the US. HAIs are responsible for more deaths in the United States than the top leading causes of death.

These infections, hospitalizations, intangibles, such as grief and anxiety, and dollars spent are all preventable.

An important predisposing factor to HAIs is the use of instrumentation or devices for intubation, delivery of therapeutic agents, or drainage of body fluids during patient care as supportive measures. HAIs often consist of device-related infections, i.e. catheter-associated urinary tract infections, vascular catheter-associated infections, and ventilator-associated pneumonias. Unlike other hospital-acquired infections device-related infections are linked directly to medical care.

The basic principles of infection control include (i) removing sources of infection by treating infections and decontamination procedures; (ii) preventing transfer with good hand hygiene, aseptic procedures, and appropriate isolation; (iii) enhancing resistance with good nutrition, and appropriate antibiotic prophylaxis or vaccination.

There are other key policies important in the control of HAIs, which include policies that will reduce the infection risk from use of catheters, tubes, cannulas, and those regarding the prudent use of antibiotics. However, infection control is a complex problem. For example, HAIs risks are greatly increased by extensive movement of patients in the hospital, by high bed occupancy, and by an absence of facilities to isolate infected patients.

Nosocomial infections occurring in intensive care units (ICUs) are particularly worrisome because they affect immuno-compromised and fragile patients and are caused by increasingly resistant microorganisms. Patients affected with nosocomial infections thus often require the use of broad-spectrum antibiotics.

However, the use of such broad-spectrum antibiotics has led to the emergence of multi-resistant organisms.

Moreover, three key factors undoubtedly contribute to worsen this medical concern: 1) an increasing aging population; 2) a larger usage of intensive care units (ICU), hence a greater number of patients admission in ICUs; and 3) a considerable increase in the number of patients requiring mechanical ventilation.

Thus, in the absence of new effective preventive measures, one may forecast that not only the incidence of ICU-acquired infections, and in particular ICU-acquired pneumonia will inexorably rise, but also that these infections will also become increasingly difficult to treat.

In consequence, there is a high risk in the future to be faced with more fragile patients under mechanical ventilation, more ICU-acquired infections in general, and pneumonia in particular, and less available effective antibiotics to treat them.

It is thus of vital importance to dispose of new antibacterial strategies, including antibacterial strategies that may be used in a preventive manner.

Among these antibacterial strategies, targeting adhesion of the bacteria responsible for the infections offers interesting advantages, as bacterial adhesion to host cells is a necessary and vital step for bacteria to carry out their infectious process. This fundamental early phase of almost any bacterial disease requires physical contact between the invading bacterial cells and surface patient's cells, the said cell-cell contact being followed by the adhesion of the bacteria cells to the said host cell surface.

It is commonly admitted in the art, such as in Scannapieco et al. (Dentistry today 2003, vol. 22, no. 8, 79-83), that colonisation of the oropharynx is the first step leading to ICU-acquired infections, and in particular ICU-acquired pneumonia, with changes in the normal oropharyngeal flora due to the emergence of bacteria causing nosocomial respiratory infections, in particular nosocomial pneumonia. Tracheobronchial colonization with these pathogenic bacteria is the second step. The ultimate stage is often the subsequent bacterial invasion of lung parenchyma.

Preventing oropharyngeal contamination would thus also prevent the development of an ICU-acquired infection, as for example an ICU-acquired pneumonia.

Oropharyngeal colonization with Enterobacteriaceae, including *E. coli*, has been long known as the first step toward bacteria, and in particular Gram-negative bacteria, ventilator-associated pneumonia.

*Pseudomonas aeruginosa* and *Staphylococcus aureus*, among others discussed here-after, are also known as being responsible for nosocomial respiratory infections.

Numerous therapeutic strategies and drugs of oropharyngeal decontamination are already available. However, all have caveats and drawbacks. The most commonly used is mouth wash with chlorhexidine, although conflicting results surround its efficacy (Pineda et al. 2006. Crit. Care. 10:R35; Chlebicki et al. 2007. Crit Care Med., 35:595-602; Chan et al. 2007, Bmj. 334:889. Epub 2007 Mar. 26). The most potent strategy combines topical administration of non-absorbable antibiotics, although serious concerns regarding emergence of resistance have been raised, which is why its widespread use is not recommended.

There is thus a need for antibacterial compounds or substances that would inhibit adhesion of oropharyngeal bacteria causing nosocomial respiratory infections to the surface of oropharyngeal epidermis cells of the patients as well as antibacterial compounds or substances that would inhibit adhesion of oropharyngeal bacteria causing nosocomial respiratory infections to the surface of medical instruments.

Such compounds or substances would ideally allow preventing bacterial colonization of the oropharyngeal epidermis by bacteria causing nosocomial respiratory infections, in particular nosocomial pneumonia, and thus prevent the corresponding bacterial respiratory infections, and especially ICU-acquired infections, including ICU-acquired pneumonia.

There is also a need for antibacterial compounds or substances that would inhibit growth and/or virulence of oropharyngeal bacteria causing nosocomial respiratory infections. Such effects allow lowering the risk of colonization of the oropharynx and thus of developing the corresponding bacterial respiratory infections, and especially ICU-acquired infections, including ICU-acquired pneumonia, and also allow lowering the severity and thus mortality rate of these respiratory infections.

There is thus a need for antibacterial compounds or substances that would inhibit adhesion, growth and/or virulence, and preferably adhesion, growth and virulence, of oropharyngeal bacteria causing nosocomial respiratory infections.

SUMMARY OF THE INVENTION

The present invention aims notably at preventing and/or at treating respiratory infections due to bacteria causing nosocomial respiratory infections in patients requiring mechanical ventilation.

According to the inventors' experimental results, cranberry proanthocyanidins may be used for preventing colonization of oropharyngeal tissues and/or of oropharyngeal material by bacteria causing nosocomial respiratory infections.

Cranberry proanthocyanidins are described in Feghali et al. (J. Agric. Food Chem. 2012, 60, 5728-5735) as being effective against periodontal diseases such as gingivitis and periodontitis.

They are also evaluated in Vu Dang La et al. (Phytother. Res. 2009, 23, 1449-1452) for their capacity to protect macrophages and oral epithelial cells against cytotoxicity induced by bacterial components.

The present invention relates to a pharmaceutical composition comprising a cranberry-derived proanthocyanidin extract for use in locally reducing oropharyngeal colonization of bacteria causing nosocomial respiratory infections, in a mammal.

A cranberry-derived proanthocyanidin extract, or cPAC, notably possesses the following advantageous properties:
(i) the proanthocyanidins are well tolerated by individuals. Notably, an accidental ingestion of cranberry-derived proanthocyanidins will not cause any health problem;
(ii) their inoccuity allows their administration at high dosages as well as their local administration at high amounts or at high concentrations;
(iii) cranberry-derived proanthocyanidins do not present any palatability and/or acceptability difficulties; and
(iv) as already mentioned, cranberry-proanthocyanidins present a very limited risk, or even no risk, of emergence of bacterial resistance.

According to these properties, a composition according to the invention comprising a cranberry-derived proanthocyanidin extract can inhibit, in vitro, ex vivo or in vivo:
the adherence of bacteria causing nosocomial respiratory infections to the surface of oropharyngeal epithelial cells prior to or concurrently with the said bacteria entering into contact with the said cells;
the growth of bacteria causing nosocomial respiratory infections; and
the virulence of bacteria causing nosocomial respiratory infections.

The present invention also relates to a pharmaceutical composition comprising a cranberry-derived proanthocyanidin extract for use in in vivo inhibiting adherence of bacteria causing nosocomial respiratory infections to the surface of oropharyngeal epithelial cells in a mammal.

In particular, a pharmaceutical composition comprising cranberry-derived proanthocyanidin extract according to the invention is for use in in vivo inhibiting adherence, growth and/or virulence, more particularly adherence, growth and virulence, of bacteria causing nosocomial respiratory infections.

More particularly, a cranberry-derived proanthocyanidin extract (or cPAC) or compositions comprising the same according to the invention are useful in the prophylaxis or treatment of oropharyngeal and/or lung diseases mediated by bacteria causing nosocomial respiratory infections.

The present invention thus also concerns a pharmaceutical composition comprising a cranberry-derived proanthocyanidin extract for use in preventing and/or treating lung infection by bacteria causing nosocomial respiratory infections, in a mammal.

As shown in the following examples, a cranberry-derived proanthocyanidin extract unexpectedly exhibit an inhibitory effect on bacterial growth and adherence of different strains of bacteria causing nosocomial respiratory infections as well as a significant inhibitory effect on virulence of these bacteria.

The effect of a cranberry-derived proanthocyanidin extract is more particularly interesting in that it has no bactericidal effects, but only bacteriostatic ones, thus preventing the emergence of multi-resistant bacteria.

The inventors have indeed confirmed that despite an early and dose-dependent inhibition of *E. coli* growth, viability of bacterial cells was preserved after cPAC exposure. Indeed, bacteria were able to grow normally when cPAC was removed despite the strong inhibitory effects observed in terms of adhesion, virulence and growth.

The same applies to the other bacteria tested in the present invention.

The present invention also relates to a method for preventing colonization of an oropharyngeal material by bacteria causing nosocomial respiratory infections, the method comprising bringing into contact a composition comprising a cranberry-derived proanthocyanidin extract on at least a part of the surface area of the said material.

The present invention moreover provides the advantage of improving tolerance and acceptability of the treatment by the patients as discussed previously.

FIGURES' LEGENDS

FIGS. 1 to 8: Growth curves for eight *Escherichia coli* strains (No 1 to 8) illustrated in Table 1 grown in different conditions of cranberry-derived proanthocyanidin extract (cPAC) concentrations: 0, 50, 250, 500 or 1000 µg/mL. Abscissa: time after addition of cranberry-derived proanthocyanidin extract to the culture medium of the 8 tested strains of *Escherichia coli* as expressed in hours:minutes:seconds (h:m:s). Ordinate: absorbance measurement at 600 nanometers.

FIGS. 9 to 16: Growth curves for eight different strains of bacteria causing nosocomial infections (Extended-spectrum beta-lactamase-producing *E. coli* strain and strains of *Enterobacter cloacae, Klebsiella pneumonia, Pseudomonas aeruginosa, Acinetobacter baumannii*, the strain *Staphylococcus aureus* ATCC ITO and the strain *Staphylococcus aureus* WM2) grown in different conditions of cranberry-derived proanthocyanidin extract concentrations: 0, 50, 250, 500 or 1000 µg/mL. Abscissa: time after addition of cranberry-derived proanthocyanidin extract to the culture medium of the 8 tested strains as expressed in hours: minutes:seconds (h:m:s). Ordinate: absorbance measurement at 600 nanometers.

Figure 17:
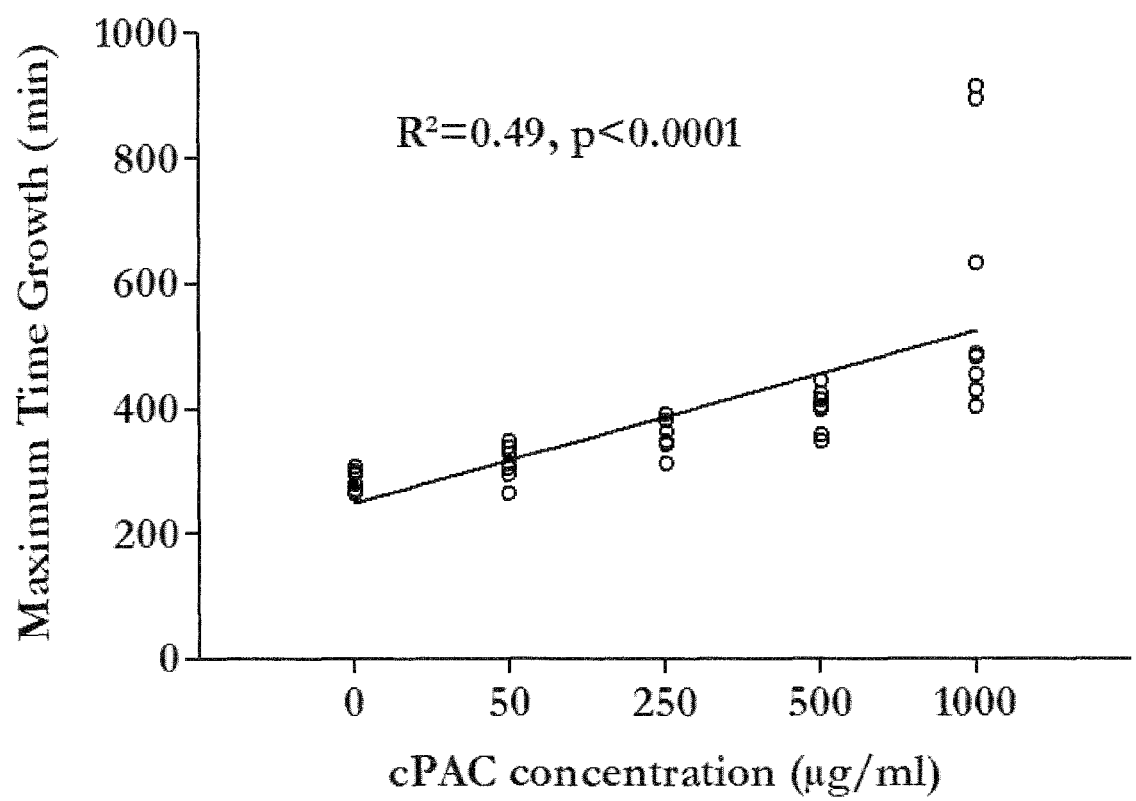

FIG. 17: linear regression of maximal time growth to cPAC concentration (µg/mL). The maximal time necessary to achieve the Maximal Growth Rate (MGR) for each one of the eight *Escherichia coli* strains numbered 1 to 8 in all the tested conditions of cranberry-derived proanthocyanidin extract (cPAC) concentrations: 0, 50, 250, 500 or 1000 µg/mL are represented. Abscissa: cranberry-derived proanthocyanidin extract concentrations: 0, 50, 250, 500 and 1000 µg/mL; Ordinate: maximal time necessary to achieve MGR in minutes. $R^2$ value=0.49, $p<0.0001$.

Figure 18:
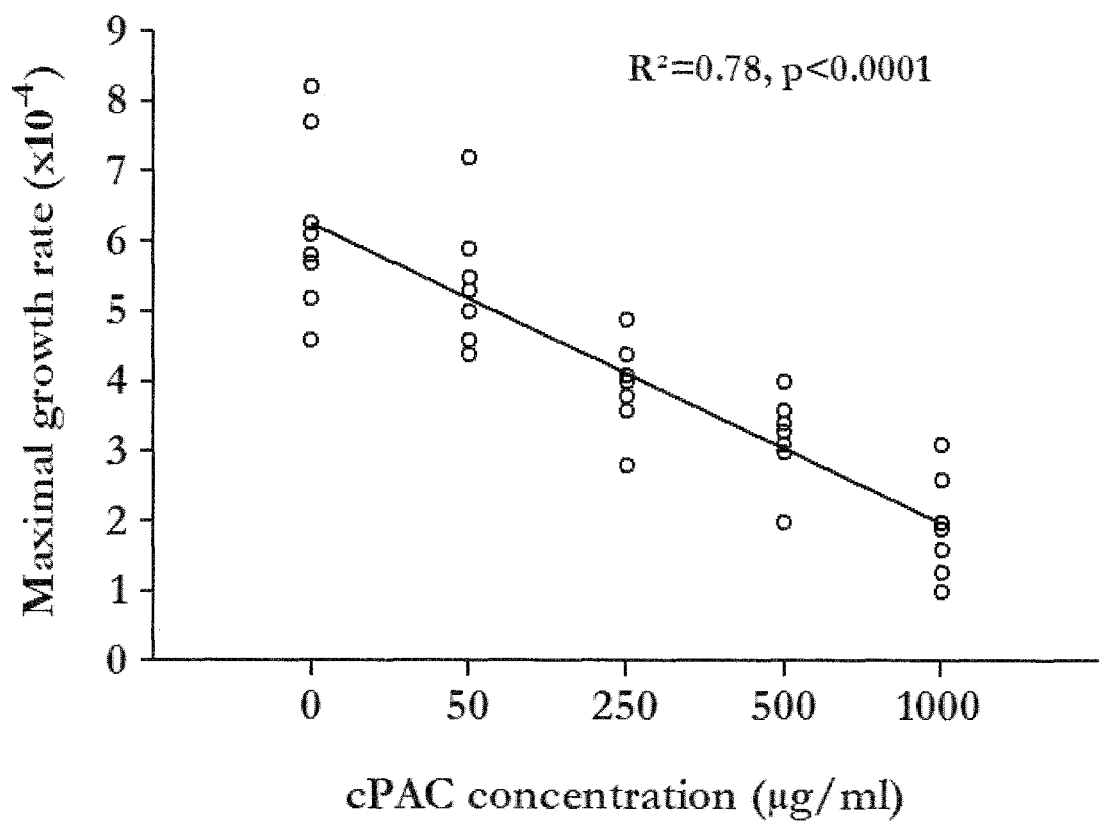

FIG. 18: linear regression of maximal growth rate (MGR) ($10^{-4}$) to cPAC concentration (g/mL). The Maximal Growth Rate for each one of the eight *Escherichia coli* strains numbered 1 to 8 in all the tested conditions of cranberry-derived proanthocyanidin extract (cPAC) concentrations: 0, 50, 250, 500 or 1000 µg/mL are represented. Abscissa: cranberry-derived proanthocyanidin extract concentrations: 0, 50, 250, 500 and 1000 µg/mL; Ordinate: maximal growth rate ($\times 10^{-4}$). $R^2$ value=0.78, $p<0.0001$.

Figure 19:
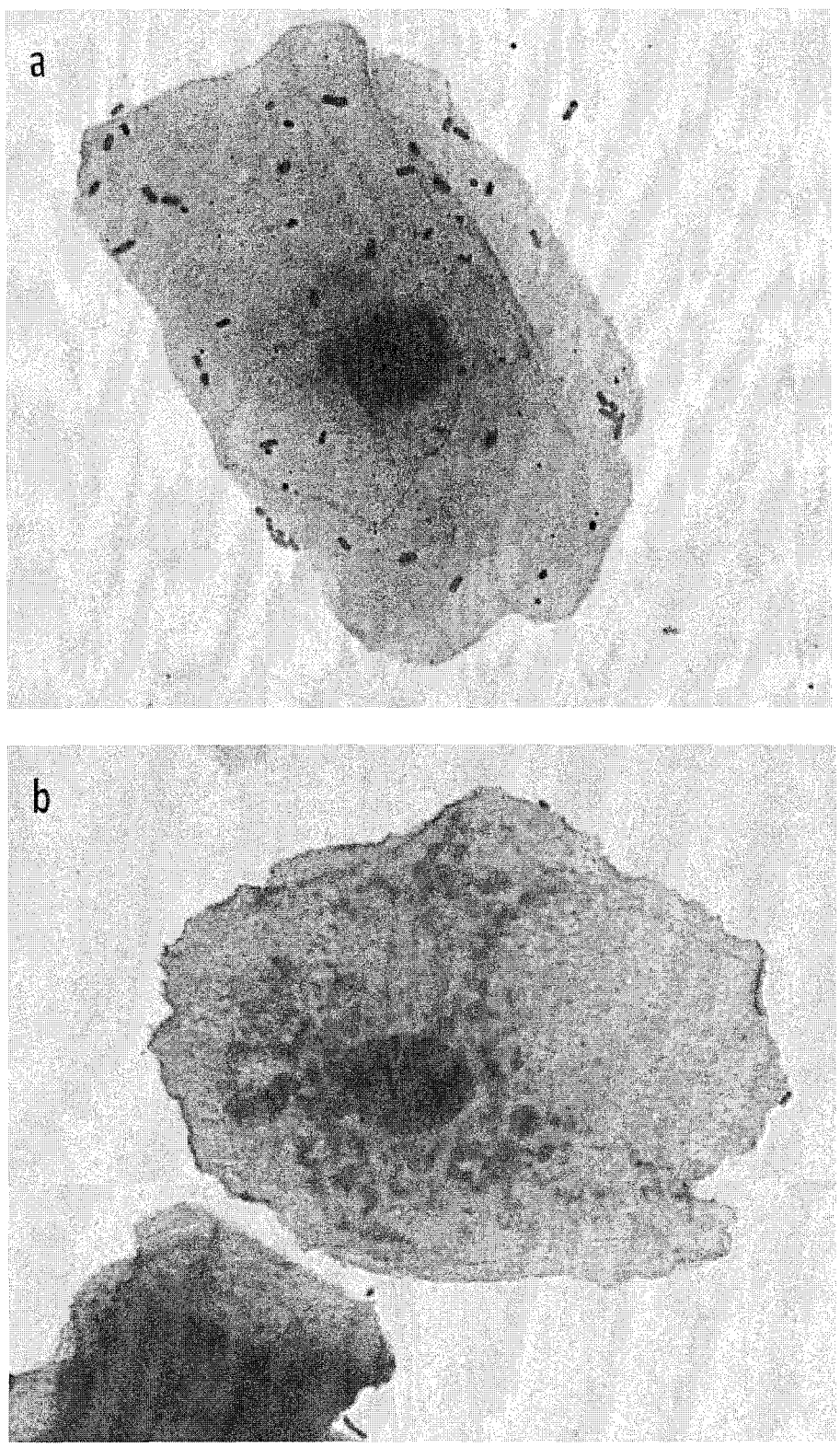

FIG. 19: Optical microscopy (×1000 magnitude) showing a fresh buccal epithelial cell:
(a) in the absence of cPAC. Presence of numerous rods (*E. coli*) on the surface of the cell;
(b) in the presence of 180 µg/mL of cPAC. Presence of only one or two rods on the surface of the cell is observed.

Figure 20:
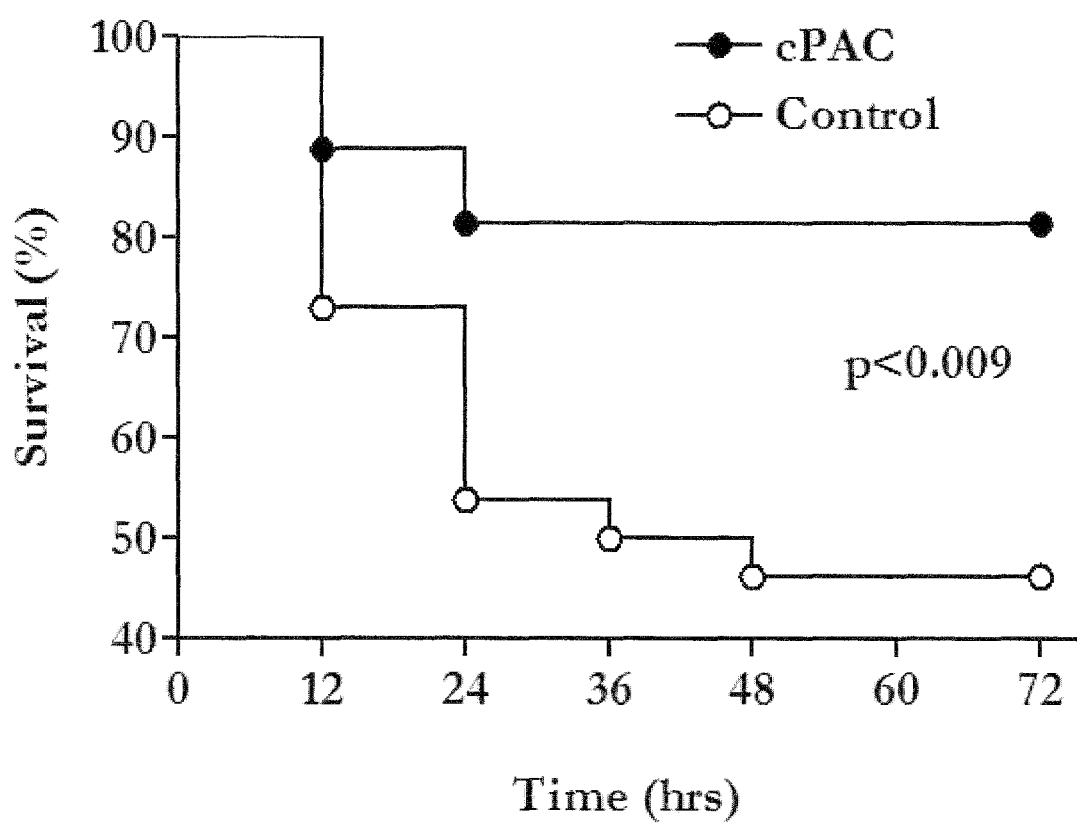

FIG. 20: illustrates the Kaplan-Meir survival curves of mice that have been challenged with *E. coli* strains numbered 1 to 8 in the absence of cranberry-derived proanthocyanidin (○) or challenged with *E. coli* strains numbered 1 to 8 in the presence of cPAC (●). Abscissa: time after challenged as expressed in hours. Ordinate: percent survival ($p<0.009$).

Figure 21:
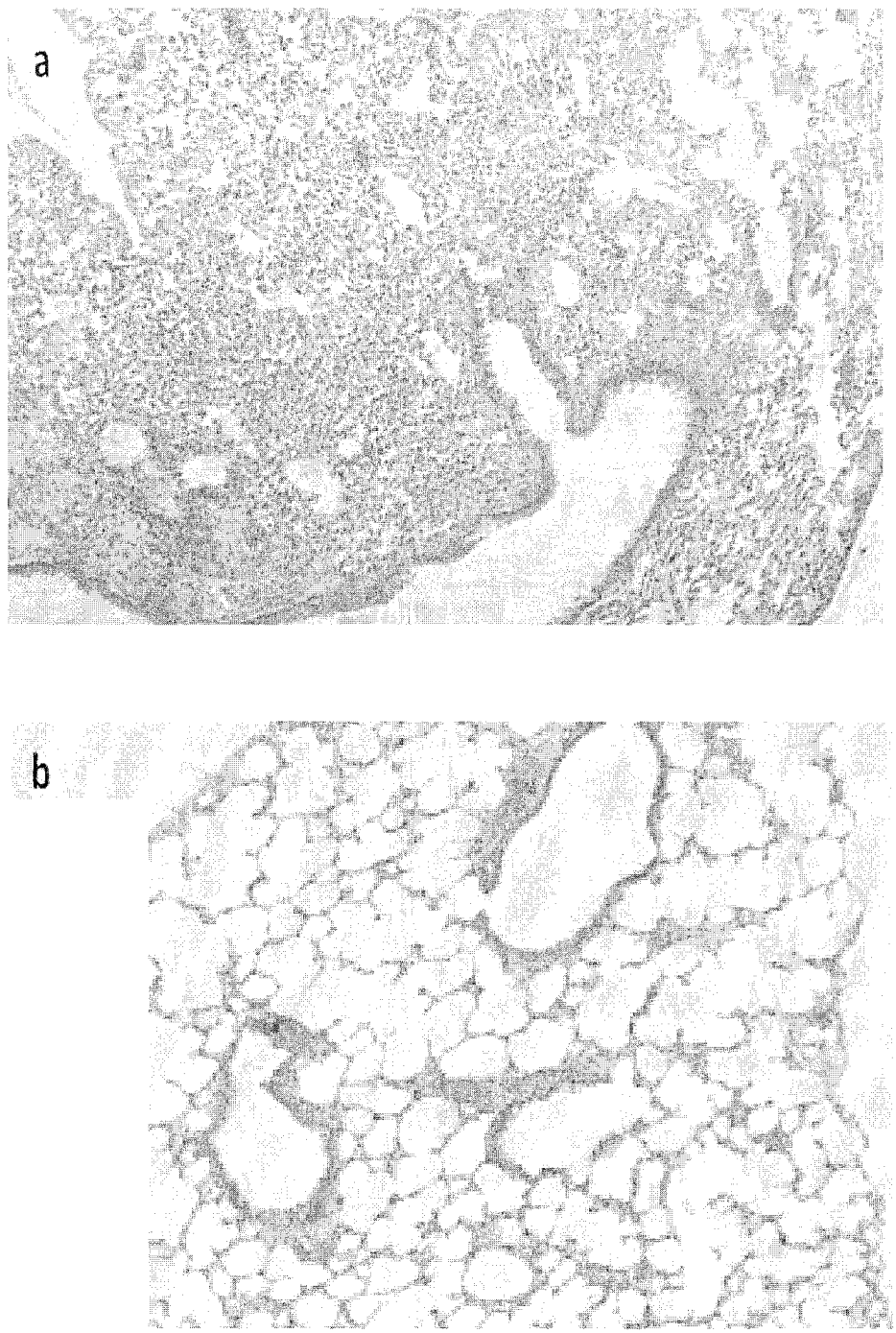

FIG. 21: Histopathology of representative mice lungs after challenge with (a) non-exposed *E. coli* strains numbered 1 to 8 or (b) cPAC-exposed *E. coli* strains numbered 1 to 8.

Figure 22:
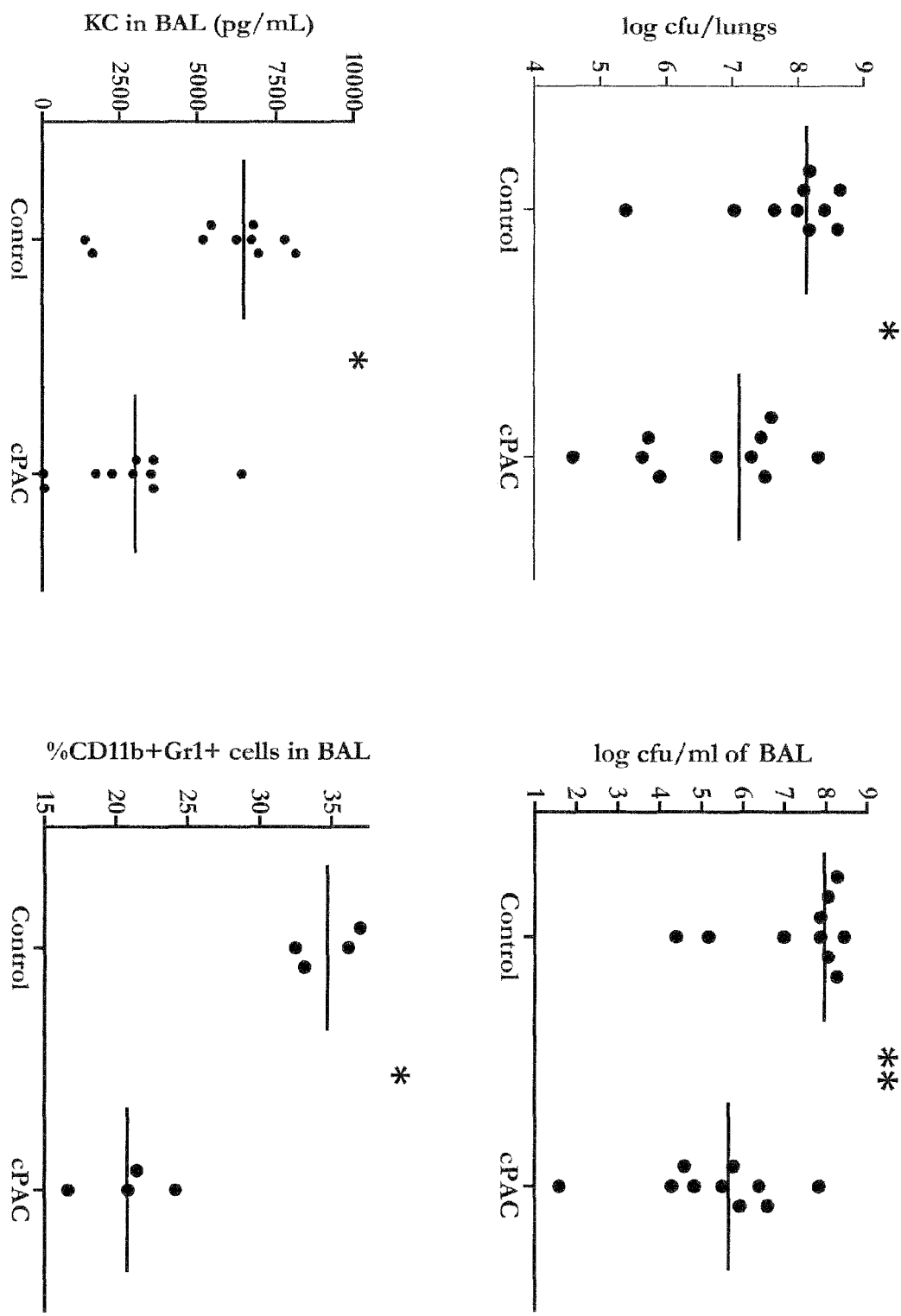

FIG. 22: Effects of cPAC on bacterial counts, KC concentrations and polymorphonuclear recruitment at the early stage of a bacterial pneumonia.
  a: Bacterial counts in homogenized lungs. Abscissa: log cfu/lungs. Ordinate: Control or cPAC results. Mann-Whitney test: *$p<0.05$.
  b: Bacterial counts in BAL. Abscissa: log cfu/lungs. Ordinate: Control or cPAC results. Bacterial exposition to cPAC decreased bacterial counts in homogenized lungs and in BALs. Mann-Whitney test: **$p<0.01$.
  c: KC concentrations in BALs. Abscissa: log cfu/lungs. Ordinate: Control or cPAC results. KC values were lower after cPAC exposition. Mann-Whitney test: *$p<0.05$.
  d: Proportion of polymorphonuclear cells (CD11b+Gr1+ F4/80– cells) in BALs. Instillation of cPAC-exposed *E. coli* induced less polymorphonuclear recruitment that instillation with control *E. coli*. Mann-Whitney test: *$p<0.05$.

Figure 23:
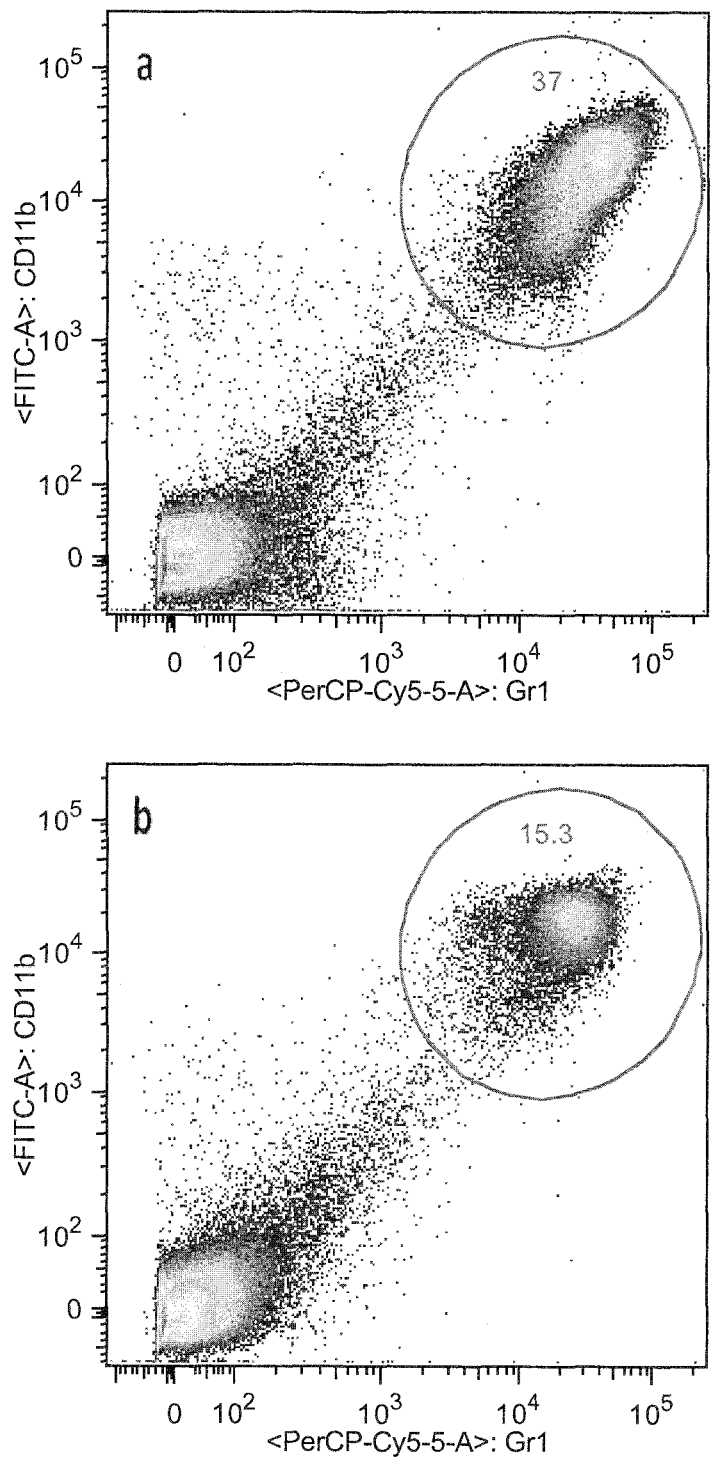

FIG. 23: FACS analysis. Y-axis represents anti-CD11b antibody and X-axis anti-Gr1 antibody. The two panels are representative of one mouse in each group. All bronchoalveolar cells were F4/80 negative. Polymorphonuclear (PMNs) cells (CD11b$^{high}$ Gr1$^{high}$ F4/80$^{low}$) were gated in BAL of infected mice 8 hours after instillation with $3.6 \times 10^8$ cfu *E. coli* cultured overnight without (a) or with 180 µ/ml cPAC (b). On these graphs, PMNs represented 37% of BAL cells in the control mouse (a) and only 15.3% of BAL cells when *E. coli* was treated with cPAC (b). As shown on FIG. 22d, the proportion of PMNs was significantly lower when instilled bacteria had been previously treated with cPAC.

DETAILED DESCRIPTION OF THE INVENTION

Definitions

As used herein:
"oropharyngeal" or "oropharynx" refers to the part of the respiratory tract going from the soft palate to the level of the hyoid bone including the oral cavity (teeth, gums, tongue, interior wall of cheeks).
"Gram-negative bacteria" refers to bacteria having an outer lipid membrane. Gram-negative bacteria are stained in pink according to the conventional Gram staining technique.
"patient" is intended for a human or non-human mammal affected or likely to be affected with a condition associated with a bacterial infection of the respiratory tract according to the invention. Said patient is preferably a human being.
"Cranberry-derived proanthocyanidin extract", as used herein, mean a mixture of oligomers and polymers composed of flavan-3-ol repeating units linked through $C_4$-$C_8$, $C_4$-$C_6$ bonds which are obtained from cranberry (*Vaccinium macrocarpon*)
"respiratory infections" is intended for bacterial infections in any place of the respiratory tract, for example the lungs, larynx, pharynx, oropharynx, nasopharynx, laryngopharynx, trachea, bronchus and bronchioles.

The present inventors have performed a huge amount of work with the view of identifying substances endowed with properties of inhibiting adhesion, virulence and growth of bacterial cells causing nosocomial respiratory infections.

The inventors have unexpectedly found herein that cranberry proanthocyanidins exhibit these three important properties, i.e. anti-adhesive, anti-virulence and anti-growth properties on oropharyngeal pathogenic bacteria causing nosocomial respiratory infections. As shown in the following examples, the inventors advantageously discovered that a cranberry-derived proanthocyanidin extract significantly reduces bacterial adhesion on oropharyngeal cells, virulence and growth of different strains of pathogenic bacteria causing nosocomial respiratory infections.

It is shown herein that cranberry proanthocyanidins interfere only with the bacterial attachment to host cells or to material surfaces, and with the virulence and growth of these bacteria, without exerting a direct bactericidal activity. Then, the use of cranberry proanthocyanidins as an antibacterial agent against bacteria causing nosocomial respiratory infections shall not induce bacterial resistance towards this active agent.

It is shown herein that a cranberry-derived proanthocyanidin extract inhibits adhesion of bacteria causing nosocomial infections to oropharyngeal mammal cells, in particular oropharyngeal human cells.

Cranberry-derived proanthocyanidins were already known in the art for their ability to inhibit adherence of *Escherichia coli* strains exhibiting type 1 and P fimbriae to uroepithelial cells (Howell et al. 1998 N. Engl. J. Med., 339:1085-1086; and Lai Yeap Foo et al. (2000, Phytochemistry, 54, 173-181)). This adherence inhibition property has formed the basis to the usage of cranberry extracts to prevent urinary tract infections.

Cranberry-derived proanthocyanidins were also described in O'May Che et al. (Appl. Environ. Microbiol. 2011, vol. 77, no. 9, 3061-3067) as blocking the swarming motility of *Pseudomonas aeruginosa*.

They were also described in combination with ascorbic acid in a nasal and pharyngeal spray solution as eliminating the yeast *Candida* from the upper air and food passages and as having an anti-viral activity.

In 2008, a Cochrane meta-analysis (Jepson R G, and Craig J C. 2008. Cochrane Database Syst Rev.:CD001321) concluded there was some evidence that cranberry juice may decrease the number of symptomatic UTIs over a 12 months period, particularly for women with recurrent UTIs.

On the contrary, the update of 2012 (Jepson R G, Williams G, and Craig J C. 2012. Cochrane Database Syst Rev 10:CD001321) concluded that cranberry juice is less effective than previously indicated. Moreover, many studies reported low compliance and high withdrawal/dropout problems which they attributed to palatability/acceptability of the products, primarily the cranberry juice (Beerepoot et al. 2011. Arch Intern Med 171:1270-8; Gurley B J. 2011. Arch Intern Med 171:1279-80).

Moreover, Kylli et al. (J. Agric. Food Chem. 2011, 59, 3373-3384) concluded that polymeric proanthocyanidin extracts of lingonberries and cranberries were strongly anti-microbial against *Staphylococcus aureus*, whereas they had no effect on other bacterial strains such as *Salmonella* enteric sv. *Typhimurium*, *Lactobacillus rhamnosus* and *Escherichia coli*.

However, according to the knowledge of the inventors, it has so far never been considered or disclosed that Cranberry-derived proanthocyanidin extract can be effective in inhibiting the adherence, virulence and growth of bacteria causing nosocomial respiratory infections.

To the best of the inventors' knowledge, the adhesion of clinical isolates of *E. coli* responsible for pulmonary colonization or infection on fresh human oral cells, namely fresh oral epithelial cells, is disclosed for the first time herein.

Because *E. coli* isolates responsible for ventilator-associated pneumonia harbour more virulence factor genes than those responsible for colonization only, the present inventors believe that the uses of cranberry-derived proanthocyanidin extract that are disclosed herein are of important clinical usefulness.

The context of oropharyngeal decontamination, more particularly for patients in intensive care units (ICU), is highly advantageous compared to already known urinary tract infections prevention, as much greater concentrations of Cranberry-derived proanthocyanidin extract can be applied locally without requiring ingestion of important quantities of liquid.

Cranberry-Derived Proanthocyanidin Extract

Proanthocyanidin, also known as condensed tannins, are sugar free condensed flavans composed of catechin and epicatechin monomers, leading to anthocyanidin when depolymerised under oxidative conditions, and are mostly known for their antioxidant properties.

They are naturally occurring plant metabolites widely available in fruits, vegetables, nuts, seeds, flowers, and bark. Proanthocyanidin can in particular be found in many woody plants, such as grape seeds and cranberries, as well as in white pine, blackjack oak, horse chestnut, witch hazel and hawthorn black bark, apples, barley, chocolate, rhubarb, rose hips leaves of bilberry, birch and ginkgo.

Also known as procyanidins, these substances are the main precursors of the blue-violet and red pigments in plants. These compounds are part of a specific group of polyphenolic compounds—the flavonoids.

There are different proanthocyanidin types that differ in view of the intermolecular bonds between the monomers, called A-type (one intermolecular bond) or B-type (two intermolecular bonds) linkages, and in view of their degree of polymerization.

Cranberry-derived proanthocyanidins have been identified as having the extension units of epigallocatechin, catechin, epicatechin, proanthocyanidin A2 dimer, and proanthocyanidin A type trimer, and the terminal units of catechin, epicathecin, proanthocyanidin A2 dimer and proanthocyanidin A type trimer (Jungmin lee, J. Funct. Foods, January 2013, 144-163).

According to one embodiment, a cranberry-derived proanthocyanidin extract according to the invention is obtained from *Vaccinium macrocarpon*, in particular its flowers, root, leaf, stem or fruit.

A method to obtain a cranberry-derived proanthocyanidin extract according to the invention is indicated in Feldman et al. BMC Complement. Altern. Med. 2012, 12:6 or in Babou et al. J. Biomed. Biotechnol. 2012, Vol. 2012, Article ID 590384.

For example, a cranberry-derived proanthocyanidin extract can be obtained by isolation from cranberry fruit using solid-phase chromatography (Howell et al. J Dent. Res. 2009, 88(7):627-632).

Further examples of methods to obtain cranberry-derived proanthocyanidin extracts are illustrated, mutatis mutandis, in the chapter entitled "Preparation of pine needle extracts" in Nam-Young Kim et al., Nutr. Res. Pract. 2010; 4(1):16-22.

A cranberry-derived proanthocyanidin extract can also be obtained from food products as illustrated in Howell et al. Phytochemistry 2005 September; 66(18):2281-91.

The amount of proanthocyanidin in a cranberry-derived proanthocyanidin extract can be determined by various methods known from the man skilled in the art, such as the method of Brand-Williams et al. (Lebensm Wiss Technol 1995; 28:25-30).

Such a method can for example be determined in a cranberry-derived proanthocyanidin extract by dissolving the extract and diluting it in 99% methanol. One milliliter of diluted extract is then added to 6 mL of 5% (v/v) HCl (in butanol) solution and 0.2 mL of $FeNH_4(SO_4)_2$—$H_2O$ (in 2M HCl) solution. The sample mixture is then incubated at 95° C. for 40 minutes and then centrifuged at 14,000×g for 5 minutes. The supernatant is transferred to a new vial and 5% (v/v) HCl (in butanol) solution is added. The absorbance is then measured at 550 nm and the amount of proanthocyanidin is calculated on the basis of a reference curve.

A cranberry-derived proanthocyanidin extract has the advantage of being non-toxic, even when administered at high doses. Indeed, studies have determined that the LD50 in rats is greater than 4000 mg/kg (Schulz et al. Rational Phytotherapy: A physicians' Guide to Herbal Medicine. Berlin: Springer, 1997:306).

Moreover, no chronic toxicity has been reported to the knowledge of the inventors and it has been demonstrated (Yu C Food Chem Toxicol 1987; 25:135-40) that proanthocyanidins demonstrate no significant mutagenicity as giving up to 60 mg/kg daily to rats and dogs for up to 12 month did not result in any significant toxicity.

A composition according to the invention can contain cranberry-derived proanthocyanidin extract in a concentration of at least 50 μg/mL, in particular at least 180 μg/mL, preferably at least 250 µg/mL, in particular at least 500 µg/mL, more particularly at least 1000 µg/mL.

Bacteria Causing Nosocomial Respiratory Infections

The present invention aims at inhibiting and/or reducing adherence, growth and virulence of bacteria implicated in respiratory tract infections, and in particular in oropharyngeal and lung infections.

As indicated previously, bacteria concerned by the present invention are those specifically involved in respiratory tract infections through oropharyngeal colonization. They are notably responsible for pulmonary colonization or infection on oropharyngeal cells and are becoming increasingly prevalent in particular in ventilator-associated pneumonia. Their adhesion to the oropharynx is an obligatory step before lung infection.

Such bacteria according to the invention can be Gram-negative or Gram-positive bacteria.

A Gram-positive bacterium according to the invention is in particular *Staphylococcus aureus* (*S. aureus*).

According to an embodiment of the invention, a bacterium causing nosocomial respiratory infections is selected from Gram-negative bacteria.

A Gram-negative bacterium according to the invention can be selected from the group comprising, but not limited to, Enterobacteriaceae (including *Escherichia coli, Enterobacter cloacae* and *Klebsiella pneumonia*), *Pseudomonas aeruginosa* (*P. aeruginosa*), *Acinetobacter baumannii* (*A. baumannii*).

According to an embodiment of the invention, a bacterium causing nosocomial respiratory infections is selected from Enterobacteriaceae bacteria.

An Enterobacteriaceae bacterium according to the invention is in particular selected from the group comprising, but not limited to, *Escherichia coli* (*E. coli*), *Enterobacter cloacae* (*E. cloacae*) and *Klebsiella pneumoniae* (*K. pneumoniae*), and is in particular *Escherichia coli*.

An *Escherichia coli* according to the invention can be an extended-spectrum Beta-lactamase-producing *Escherichia coli*.

According to an embodiment of the invention, a bacterium causing nosocomial respiratory infections is selected in the group comprising Gram-negative bacteria and *Staphylococcus aureus*.

According to an embodiment of the invention, a bacterium causing nosocomial respiratory infections is selected from the group comprising Enterobacteriaceae bacteria, *Pseudomonas aeruginosa, Acinetobacter baumannii* and *Staphylococcus aureus*.

According to an embodiment of the invention, a bacterium causing nosocomial respiratory infections is selected from the group comprising *Escherichia coli, Enterobacter cloacae, Klebsiella pneumoniae, Pseudomonas aeruginosa, Acinetobacter baumannii* and *Staphylococcus aureus*.

Compositions

As indicated previously, the present invention aims at providing compositions intended to be put into contact with oropharyngeal cells and compositions intended to be put into contact with oropharyngeal material.

Thus according to a first embodiment, the present invention concerns a composition intended to be put into contact with oropharyngeal cells or tissues.

A pharmaceutical composition according to the invention, comprising a cranberry-derived proanthocyanidin extract, can be used:

in locally reducing oropharyngeal colonization of bacteria causing nosocomial respiratory infections, in a mammal;

in preventing and/or treating lung infections by bacteria causing nosocomial respiratory infections;

in in vivo inhibiting adherence of bacteria causing nosocomial respiratory infections to the surface of oropharyngeal epithelial cells in a mammal;

in in vitro or ex vivo inhibiting adherence of bacteria causing nosocomial respiratory infections to the surface of oropharyngeal epithelial cells; and/or in in vitro, inhibiting growth of a bacteria causing nosocomial respiratory infections.

According to this embodiment, a composition of the invention is applied to the soft tissues of the back of the mouth, and/or the throat, in particular to the soft palate at the rear of the mouth, to the uvula, inside of the cheeks, to the back of the tongue and/or the upper part of the pharynx, to the teeth and/or the gums.

According to this embodiment, a cranberry-derived proanthocyanidin extract is present in a composition of the invention in a concentration of at least 50 µg/mL.

Preferably, a cranberry-derived proanthocyanidin extract is present in a composition of the invention in a concentration of at least 180 µg/mL, in particular at least 250 µg/mL, in particular at least 500 µg/mL, more particularly at least 1000 µg/mL.

According to an embodiment of the invention, a pharmaceutical composition according to the invention comprises the cranberry-derived proanthocyanidin extract in a concentration adapted for administration of the cranberry-derived proanthocyanidins in an amount of between 15 and 500 mg daily to an individual, preferably in an amount of between 40 and 300 mg daily to an individual, more particularly in an amount of between 80 and 150 mg daily to an individual.

The quantity of cranberry-derived proanthocyanidin extract administered and thus the quantity of pharmaceutical composition according to the invention administered to an individual in need thereof can vary over time.

For example, when a cranberry-derived proanthocyanidin extract or a composition according to the invention is administered to said individual over a long period of time, the treatment can be separated between a first acute treatment phase where the individual is frequently, for example daily, administered with a high amount of said extract or composition, followed by a maintenance treatment phase, where a lower quantity of said extract or composition is administered to said individual and/or where the frequency of administration is reduced compared to the acute treatment phase.

The pharmaceutical composition can be in a form selected from the group consisting of a liquid, a spray, a syrup, a gel, a foam, or a paste.

The pharmaceutical composition is preferably applied by spray to coat the aimed tissues.

The pharmaceutical composition provides the above mentioned effects for a period of at least about 6 hours after administration, preferably for a period of at least about 4 hours.

According to a preferred embodiment, the oropharyngeal cells of the patient are treated with the pharmaceutical composition continually or at a predetermined frequency, for example chosen among every 10 minutes, 30 minutes, 1 hour, 2 hours, 4 hours, 6 hours, two times a day, once a day, less than seven times a week or even less than four times a month.

As indicated previously, a cranberry-derived proanthocyanidin extract or a pharmaceutical composition according to the invention possess the same advantageous properties in terms of (i) inhibition of adhesion property on oropharyngeal cells of bacteria causing nosocomial respiratory infections, (ii) inhibition of growth of bacteria causing nosocomial respiratory infections, (iii) diminution of virulence of bacteria causing nosocomial respiratory infections, and (iv) inhibition of colonization of oropharynx by bacteria causing nosocomial respiratory infections.

Thus, an extract or a composition according to the instant invention is particularly useful for the prevention and/or treatment of pneumonia, of tracheobronchitis, of tracheal colonization.

According to a second embodiment, the present invention concerns a pharmaceutical composition intended to be put into contact with oropharyngeal material.

According to this embodiment, a cranberry-derived proanthocyanidin extract is present in a composition of the invention in a concentration of at least 50 µg/mL.

Preferably, a cranberry-derived proanthocyanidin extract is present in a composition of the invention in a concentration of at least 250 µg/mL, in particular at least 500 µg/mL, more particularly at least 1000 µg/mL.

As a treated oropharyngeal material is intended to be put into contact with oropharynx of an individual, in particular with oropharynx of patients in intensive care units, a composition according to the invention comprises a physiologically acceptable medium.

An oropharyngeal material according to the invention can be selected from the group comprising an endotracheal tube, a tracheotomy tube, a ventilator, a feeding tube, a nasogastric tube and a tongue depressor.

The composition according to this embodiment can be in a form selected from the group consisting of a liquid, a spray, a gel, a foam or a paste.

The composition is preferably applied by spray to coat at least a part of the surface area of the medical material of interest, in particular at least the part of the surface area of the medical material of interest that will enter into contact with of be in the vicinity of the oropharyngeal cells of an individual.

The composition provides the above mentioned effects for a period of at least about 6 hours after administration, preferably for a period of at least about 4 hours.

According to a preferred embodiment, the oropharyngeal material is treated every time it is used, before it is put into contact with the patient.

As indicated previously, a cranberry-derived proanthocyanidin extract or a composition according to the invention possesses the same advantageous properties in terms of inhibition of colonization of oropharyngeal material by bacteria causing nosocomial respiratory infections.

The present invention is illustrated by the following examples, given purely for illustrative purposes, with reference to the following figures.

Material and Methods

A—*Escherichia coli* Strains

Eight clinical strains of *Escherichia coli* isolated in critically-ill patients were chosen from published *E. coli* collection (Messika et al. 2012, Intensive Care Med. 38:2007-16) with respect with their:
- isolation site (rectum, oropharynx and lung);
- clinical setting (respiratory tract colonization or ventilator-associated pneumonia);
- phylogenetic group belonging; and
- virulence factor genes content.

These isolates are stocked in glycerol at −80° C.

TABLE 1

| Ref | Sample site | Phylogenetic group | Number of virulence factor genes | Experiments |
|---|---|---|---|---|
| 1 | Rectum[1] | B1 | 0 | Growth/adhesion |
| 2 | Lung[1] | A | 0 | Growth/adhesion |
| 3 | Rectum[1] | A | aer, traT, iroN | growth |
| 4 | Lung[2] | A | papC, aer, traT, iroN | growth |
| 5 | Lung[1] | B2 | aer, traT, iroN | growth |
| 6 | Rectum[1] | B2 | papC, hly, sfa, cnfl, iroN | growth |
| 7 | Lung[2] | B2 | papC, hly, aer, sfa, cnfl, iroN | growth |
| 8 | Oropharynx[2] | B2 | papC, hlyC, aer, traT, sfa, iroN, cnfl | growth/adhesion/animal model |

[1]patient with *E. coli* respiratory tract colonisation,
[2]patient with *E. coli* ventilator-associated pneumonia.

B—Other Strains

Others strains of pathogens typically involved in VAP were tested. These include:

*Pseudomonas aeruginosa* (wild-type PAO1 strain, purchased from Institut Pasteur collection, Paris, France,)

*Klebsiella pneumoniae* (clinical strain, gift from Microbiology Laboratory, Louis Mourier Hospital)

*Enterobacter cloacae* (clinical strain, Microbiology Laboratory, Louis Mourier Hospital)

ESBL secreting *E. coli*, ST 131 strain, (Clinical strain, gift from Microbiology laboratory Bicetre Hospital)

*Acinetobacter baumannii* (clinical strain, gift from Microbiology Laboratory, Louis Mourier Hospital)

3 *Staphylococcus aureus* strains (USA 300; MW2; ATCC ITO)

C—Animals

Virulence experiments were performed on pathogen free, 6-8 week-old male Balb/C mice (Janvier Labs, Le Genest Saint Isle, France) in compliance with the recommendations of the French Ministry of Agriculture and approved by the French Veterinary Services and regulatory authorization to experiment on animals.

D—Cranberry-Derived Proanthocvanidin Extract

All experiments were done with European Medicines Agency (EMEA) approved pharmaceutical cranberry (*Vaccinium macrocarpon*) dehydrated extract with standard 36 mg of cranberry proanthocyanidins (cPAC) concentration per capsule measured by BL-DMAC (Urell Pharmateuka laboratories, Rueil Malmaison, France).

I. Bacterial Growth a) Method

The behavior of 8 different *Escherichia coli* strains was studied in standard Lysogeny broth (LB-Medium BIO101Inc, Carlsbad, Calif., USA). The 8 strains concerned are those indicated in Table 1.

After a 37° C. overnight culture, isolates were centrifuged and re-suspended in PBS to obtain a concentration of $10^4$-$10^5$ cells/mL.

Growth of these different strains was tested in different conditions of proanthocyanidins concentrations (0, 50, 250, 500 and 1000 µg/ml).

Bacterial growth was monitored in a 96 well plate by automated absorbance measurements at 600 nanometers every 450 seconds for 18 hours at 37° C. in micro aerobic conditions using Tecan Infinite M200 apparatus (Tecan France SAS, Lyon, France). Bacterial growth curves were established by the Magellan Software® (Tecan France SAS, Lyon, France).

Bacterial viability after 18 hours of cranberry-derived proanthocyanidins exposure in the Tecan was controlled for each isolate and each condition by plating bacterial cultures on LB agar.

Each experiment was repeated three times and performed in three replicates.

For growth experiments analysis, the generalized linear model (GLM) procedure of SAS software has been used. A MANOVA analysis was performed to evaluate the "concentration" effect. The growth equality for all isolates and cranberry-derived proanthocyanidin concentrations were tested two by two by the contrast method. The maximal growth rate (MGR) that evaluates the minimal time for a division of a bacterial cell into two independent cells and the maximal time necessary to reach this MGR (Tmax) were calculated using R software.

b) Results

The results obtained are indicated in FIGS. 1 to 8.

Growth behaviour was evaluated by automated absorbance measurements during 18 hours and absorbance variation was expressed as the mean value+/−SD of nine repetitions for all isolates. No repetition effect was found.

A concentration dependant inhibitory effect of cranberry-derived proanthocyanidins was observed on bacterial growth of all *Escherichia coli* isolates tested.

An inhibitory effect can be seen starting from 50 µg/mL of cranberry-derived proanthocyanidins, in particular with *E. coli* strain No 8.

A more pronounced inhibitory effect was seen starting at 250 µg/mL. This effect is more particularly pronounced starting from above 500 µg/mL.

Three *E. coli* strains (No 1, 2 and 8) seemed more susceptible to cranberry with a significant inhibitory effect observed, even with the lowest cPAC concentration of 50 µg/mL.

Finally at the concentration of 1000 µg/mL of cranberry-derived proanthocyanidins, a high increase of the cranberry-derived proanthocyanidins inhibitory effect was observed.

A shifting to the right of the growth curves was observed, indicating a slowing down of the transition into the exponential phase and a near cancellation of bacterial growth for the 1000 µg/mL condition.

Concerning the stationary phase of growth, significant different bacterial concentrations were found evolving counter proportionally to the cranberry concentrations.

Moreover, when growth finally started, the exponential growth phase was shorter in presence of cPAC and bacterial cells entered their stationary phase earlier, achieving ultimately a lower biomass. These observations, quantified by calculating the maximal growth rate (MGR) and the maximal time necessary to achieve the MGR (Tmax), are represented in FIGS. 17 and 18.

A positive correlation between increasing cPAC concentrations and values of Tmax has been found when pooling all the eight strains together (FIG. 17).

Conversely, the MGR was negatively correlated with cPAC concentrations (FIG. 18).

The systematic bacteria viability control after 18 hours in the TECAN showed a normal growth in control LB for the bacteria submitted to different cranberry-derived proanthocyanidins concentrations despite the very strong growth inhibition during the cranberry exposure.

This non bactericidal activity of the cranberry-derived proanthocyanidins supports the fact that administration of cranberry-derived proanthocyanidins will significantly limit the risk of emergence of resistance in the treated bacteria.

c) Other Strains

Similar bacterial growth tests were performed with 8 other strains, i.e. an extended-spectrum beta-lactamase-producing *E. coli* strain and strains of *Enterobacter cloacae, Klebsiella pneumonia, Pseudomonas aeruginosa, Acinetobacter baumannii*, the strain *Staphylococcus aureus* ATCC ITO and the strain *Staphylococcus aureus* WM2.

The results obtained are illustrated, respectively, in FIGS. 9 to 16.

As observed with the 8 strains of *E. coli* discussed here-above, a concentration dependant inhibitory effect of cranberry-derived proanthocyanidins was also observed on bacterial growth of all these tested strains.

All these strains seemed particularly susceptible to cranberry with a significant inhibitory effect observed even with the lowest cPAC concentration of 504 mL. This is particularly visible with the extended-spectrum beta-lactamase-producing *E. coli* strain, *Klebsiella pneumonia, Pseudomonas aeruginosa* and *Acinetobacter baumannii*, and in particular *Pseudomonas aeruginosa*.

With these strains too, the exponential growth phase was shorter in presence of cPAC and bacterial cells entered their stationary phase earlier, achieving ultimately a lower biomass.

The systematic bacteria viability control after 18 hours in the TECAN showed a normal growth in control LB for the bacteria submitted to different cranberry-derived proanthocyanidins concentrations despite the very strong growth inhibition during the cranberry exposure.

This non bactericidal activity of the cranberry-derived proanthocyanidins supports the fact that administration of cranberry-derived proanthocyanidins will significantly limit the risk of emergence of resistance in the treated bacteria.

II. Buccal Epithelial Bacterial Adhesion a) Method

An ex vivo buccal epithelial cell model was used as indicated in Burke et al. 1987. J. Clin. Pathol. 40:1402-4, to test the effect of cranberry-derived proanthocyanidins on bacterial adhesion to oropharyngeal cells.

Buccal epithelial cells were obtained from four healthy volunteers by gently scraping the buccal mucosa with a sterile, soft smear brush (Rovers Medical Devices, B.V., The Netherlands) and then suspended in PBS. In every assay, buccal cells from each donor were pooled together in order to limit donor bias. They were washed and harvested by centrifugation four times and re-suspended in Roswell Park Memorial Institute (RPMI) medium at a concentration of $10^5$ cells/mL controlled by microscope count on a Kova Glasstic slide (Kove International Garden Grove, Calif.).

Three *E coli* isolates (strains No 1, 2 and 8 of Table 1) with different virulence genes content (respectively 0, 0 and 7) from different sites (rectum, lung and oropharynx respectively) and different clinical setting (simple colonization and true ventilator-associated pneumonia) were studied.

After overnight culture in standard LB at 37° C., isolates were centrifuged, washed three times and then re-suspended in PBS in order to obtain a concentration of $10^8$ bacterial cells/mL. Bacterial counts were controlled by plating on LB agar.

Buccal epithelial cells suspension was added to the bacterial strain suspension with and without cranberry-derived proanthocyanidins at a concentration of 180 µg/mL. After 30 minutes of incubation on a rotary roller at room temperature any non-adherent bacteria were removed by cyto-aspiration through an 8 µm filter (Thinprep, PAPtest filter, Cytyc corporation, Marlborogh, Mass.) and buccal cells with adherent bacteria were retained. An impression smear on a clear glass slide was then fixed in methanol. The procedure was automatically executed by a Thinprep (Cytyc corporation, Marlborough, Mass.) robot. Glass slides were then air-dried and gram-stained.

Adhesion index was calculated by inspecting 100 non-overlapping buccal epithelial cells in light microscopy and recording the number of adherent Gram-negative rods divided by the number of studied cells.

b) Results

Student t tests have been used to compare adhesion data if data were normally distributed. Otherwise, a Mann-Whitney U test was applied.

A significant reduction of bacterial adhesion on buccal cells by the cranberry juice at 180 µg/mL of cranberry-derived proanthocyanidins was found, as illustrated FIG. 19.

Reduction for the three tested strains (strains No 1, 2 and 8 of Table 1) was respectively 36%, 44% and 80%, and was statistically significant:

TABLE 2

| E. coli strains | Adhesion index | | Adhesion index reduction | p value |
|---|---|---|---|---|
| | without cPAC | with cPAC (180 µg/mL) | | |
| 1 | 22.5 +/− 8.73 | 14.5 +/− 6.49 | −36% | <0.001 |
| 2 | 25.6 +/− 11.18 | 11.2 +/− 10.91 | −44% | <0.001 |
| 8 | 44.8 +/− 16.24 | 9.7 +/− 9.39 | −80% | <0.001 |

This reduction was statistically more pronounced with isolates No 2 and 8 from lung and oropharynx compared to isolate No 1 from rectum and particularly significant with isolate No 8 from oropharynx compared to the two others.

It appears clearly that cranberry-derived proanthocyanidins significantly inhibit adhesion properties of tested bacteria, in particular those from the oropharynx and lung.

III. Bacterial Virulence a) Method

A highly virulent *Escherichia coli* isolate was chosen (isolate No 8 from Table 1). It was isolated from the oropharynx of a patient with a *Escherichia coli* ventilator-associated pneumonia and harboured 7 virulence genes.

The isolate sampled in the lung of this patient was identical to the oropharyngeal isolate, the latter being chosen in coherence with the adhesion experiments.

This isolate was incubated overnight in LB at 37° C., with and without cranberry-derived proanthocyanidins at 180 µg/mL. The two suspensions were washed, centrifuged and resuspended in PBS at a concentration of $1.8 \times 10^{10}$ cfu/mL determined by flow cytometry (Guava EasyCyte plus, Millipore Corporation, Billerica, Mass.) and systematically checked by cell count after LB agar plating.

20 µL ($3.6 \times 10^8$ cfu per mice) of the bacterial suspension were inoculated via the nasal route under light anaesthesia with Pentobarbital (Sanofi, Libourne, France) and Sevoflurane (Sevorane, Abbott, France).

Animals were closely monitored thereafter. Because preliminary experiments showed that no death occurred after 48 h, mortality was subsequently assessed until 72 hours after instillation.

b) Results

The animal experiments survival analysis were performed using Kaplan-Meier method with log-rank test for comparison of survival curves and a hazard ratio estimate (95% CI) was calculated. A p value below 0.05 was considered significant. The equality of results was tested by Cox proportional hazards test.

Preliminary experiments with a mouse model of *Escherichia coli* pneumonia referred to in Messika et al. 2012 Intensive Care Med. 38:2007-16 showed a strong correlation between the number of virulence factors carried by *E. coli* clinical isolates and mice mortality.

Preliminary data with strain No 8 which carries seven virulence factors (see Table 1), indicated that an intranasal inoculums of $3.6 \times 10^8$ cfu induced a mortality of 50 to 60%. This inoculum was chosen as it enabled to observe trends in both directions with cPAC (either an increase or a decrease in mortality). As compared to the expected 59.2% mortality of mice instilled with *E. coli* in the absence of cranberry exposure, mortality of mice challenged with the same *E. coli* strain exposed to cPAC was only 18.5%.

Exposure to cPAC led to a 69.4% reduction rate in mortality (Kaplan-Meier: p<0.001; (see FIG. 20).

FIG. 21 shows the histopathology of representative mice lungs, after challenge with non-exposed *E. coli* (FIG. 20a) or cPAC-exposed *E. coli* (FIG. 20b). A profuse neutrophil infiltration and severe alveolitis were observed in the absence of cPAC, whereas lung injury was much attenuated in mice challenged with cPAC-exposed *E. coli*.

It thus appears clearly that exposure of tested bacteria causing nosocomial respiratory infections to cranberry-derived proanthocyanidins significantly inhibits their virulence.

IV. Pathology Analysis a) Method

Additional mice were used for pathology analysis. The same pneumonia model as the one described in part III.(a) here-above was followed but mice were sacrificed 8 hours after instillation by lethal intra-peritoneal injection of Pentobarbital. Lungs were harvested and fixed for histological analysis.

For evaluation of bacterial counts and the pulmonary immune response, mice were sacrificed 8 hours after *E. coli* instillation. After exposition of the trachea, a broncho-alveolar lavage (BAL) was performed using three times one millimetre of PBS supplemented with protease inhibitor cocktail (Sigma Aldrich, St Louis, Mo.).

Lungs were then removed and homogenized in PBS.

BALs were then separated into three parts, one for bacterial counts, one for KC evaluation and one for FACS analysis.

Bacterial counts of BAL and lung homogenates were determined by serial dilutions plated on LB agar.

After centrifugation of BAL to eliminate bacterial and eukaryotic cells, KC concentrations were measured by ELISA (RayBiotech, Norcross, Ga.).

Finally, FACS analysis (LSRFortessa, BD Biosciences, San Jose, Calif.) quantified proportionally polymorphonuclear cells ($CD11b^{high}Gr1^{high} F4/80^{low}$ cells) in BALs using anti-CD11b (CD11b-FITC clone: M1/70, eBiosciences, San Diego, Calif.), anti-GR1 (Gr1-PerCP Cy 5,5 clone: RA3-6B2, BD Biosciences, San Jose, Calif.) and anti-F4/80-PE (Clone: BM8, eBiosciences, San Diego, Calif.) antibodies as described in Hall et al. Infect Immun 2008; 76:5843-5852.

Student t tests have been used to compare bacterial counts, cytokine measurements and FACS analysis data if data were normally distributed. Otherwise, a Mann-Whitney U test was applied.

b) Results

In order to observe an in vivo decrease of bacterial adhesion, the early bacterial clearance 8 hours after instillation was analyzed and the immune response of the lung at this early stage was explored.

FIG. 22a illustrates that bacterial counts were significantly decreased when exposed to cPAC in lung homogenates (Mann-Whitney test, p<0.05).

This difference was more striking in BALs of mice instilled with cPAC-exposed *E. coli* (Mann-Whitney test, p<0.01) (FIG. 22b).

This increased bacterial clearance was accompanied by a decreased inflammatory immune response of the lung since KC (keratinocyte chemoattractant) concentrations in Bronchoalveolar lavages (BALs) (FIG. 22c) and pulmonary polymorphonuclear cells (CD11b+Gr1+F4/80– cells) recruitment (FIGS. 22d and 23) were both significantly attenuated in mice instilled with cPAC-exposed *E. coli* as compared to the control group instilled with unexposed *E. coli* (Student test: p<0.01 and Mann-Whitney test: p<0.05, respectively).

In the graphics of FIG. 23, Polymorphonuclears (PMNs) cells ($CD11b^{high}$ $Gr1^{high}$ $F4/80^{low}$) represented 37% of BAL cells in the control mouse (a) and only 15.3% of BAL cells when *E. coli* was treated with cPAC (b).

The invention claimed is:

1. A method for locally reducing oropharyngeal colonization of bacteria causing nosocomial respiratory infection by inhibiting adherence of said bacteria, in a mammal, comprising
   administering to the mammal a pharmaceutical composition comprising an agent for locally reducing oropharyngeal colonization of bacteria causing nosocomial respiratory infection; and inhibiting adherence of said bacteria causing nosocomial respiratory infection, wherein said bacteria is selected from the group consisting of *Enterobacter cloacae, Klebsiella pneumoniae, Pseudomonas aeruginosa, Acinetobacter baumannii*, and *Staphylococcus aureus*;
   wherein said nosocomial respiratory infection occurs in at least one location of the respiratory tract selected from the group consisting of lung, larynx, pharynx, oropharynx, nasopharynx, laryngopharynx, trachea, bronchus and bronchiole;
   wherein the agent consists of a cranberry-derived proanthocyanidin extract obtained from *Vaccinium macrocarpon* and having an absorbance measured at 550 nm,
   wherein the agent is present in the pharmaceutical composition at a concentration in a range of 50 µg/mL to 1000 µg/mL,
   wherein the pharmaceutical composition is in a form selected from the group consisting of a liquid, a spray, a syrup, a gel, a foam, and a paste; and
   wherein the pharmaceutical composition is applied to coat oropharyngeal tissues.

2. A method for treating and/or reducing the risk of occurrence or slowing down the occurrence of lung infection by bacteria causing nosocomial respiratory infection by inhibiting adherence of said bacteria, in a mammal, comprising
   administering to the mammal a pharmaceutical composition comprising an agent for locally reducing oropharyngeal colonization of said bacteria causing nosocomial respiratory infection and inhibiting adherence of said bacteria, wherein said bacteria is selected from the group consisting of *Enterobacter cloacae, Klebsiella pneumoniae, Pseudomonas aeruginosa, Acinetobacter baumannii* and *Staphylococcus aureus*,
   wherein said nosocomial respiratory infection occurs in at least one location of the respiratory tract selected from the group consisting of lung, larynx, pharynx, oropharynx, nasopharynx, laryngopharynx, trachea, bronchus and bronchiole;
   wherein the agent consists of a cranberry-derived proanthocyanidin obtained from *Vaccinium macrocarpon* and having an absorbance measured at 550 nm,
   wherein the agent is present in the pharmaceutical composition at a concentration in the range of 50 µg/mL to 1000 µg/mL,
   wherein the pharmaceutical composition is in a form selected from the group consisting of a liquid, a spray, a syrup, a gel, a foam, and a paste; and
   wherein the pharmaceutical composition is applied to coat oropharyngeal tissues.

3. A method for reducing the risk of occurrence or slowing down the occurrence of in vivo adherence of bacteria causing nosocomial respiratory infection to a surface of oropharyngeal epithelial cells in a mammal, comprising
   administering to the mammal a pharmaceutical composition comprising an agent for locally reducing oropharyngeal colonization of bacteria causing nosocomial respiratory infection and inhibiting adherence of said bacteria, wherein said bacteria is selected from the group consisting of *Enterobacter cloacae, Klebsiella pneumoniae, Pseudomonas aeruginosa, Acinetobacter baumannii* and *Staphylococcus aureus*,
   wherein the agent consists of a cranberry-derived proanthocyanidin extract obtained from *Vaccinium macrocarpon* and having an absorbance measured at 550 nm,
   wherein the agent is present in the pharmaceutical composition at a concentration in the range of 50 µg/mL to 1000 µg/mL,
   wherein said nosocomial respiratory infection occurs in at least one location of the respiratory tract selected from the group consisting of lung, larynx, pharynx, oropharynx, nasopharynx, laryngopharynx, trachea, bronchus and bronchiole;
   wherein the pharmaceutical composition is in a form selected from the group consisting of a liquid, a spray, a syrup, a gel, a foam, and a paste; and
   wherein the pharmaceutical composition is applied to coat oropharyngeal tissues.

4. The method according to claim 1, in which the nosocomial respiratory infection is in the lung and is a pneumonia.

5. A method for reducing the risk of occurrence or slowing down the occurrence of colonization of an oropharyngeal material by bacteria causing nosocomial respiratory infection and inhibiting adherence of said bacteria, the method comprising
   contacting at least a part of a surface area of the oropharyngeal material with a pharmaceutical composition comprising an agent for locally reducing oropharyngeal colonization of bacteria causing nosocomial respiratory infection and inhibiting adherence of said bacteria, wherein the agent consists of a cranberry-derived proanthocyanidin extract obtained from *Vaccinium macrocarpon* and having an absorbance measured at 550 nm and wherein the agent is present in the pharmaceutical composition at a concentration in the range of 50 µg/mL to 1000 µg/mL;
   wherein said bacteria causing the nosocomial respiratory infection are selected from the group consisting of *Enterobacter cloacae, Klebsiella pneumoniae, Pseudomonas aeruginosa, Acinetobacter baumannji*, and *Staphylococcus aureus*;

wherein the pharmaceutical composition is in a form selected from the group consisting of a liquid, a spray, a syrup, a gel, a foam, and a paste and is applied to coat the surface area of the oropharyngeal material; and wherein the oropharyngeal material is at least one selected from the group consisting of an endotracheal tube, a tracheotomy tube, a ventilator, a feeding tube, a nasogastric tube and a tongue depressor.

6. The method according to claim 2, wherein the nosocomial respiratory infection is in the lung and is a pneumonia.

7. The method according to claim 3, wherein the nosocomial respiratory infection is in the lung and is a pneumonia.

8. The method according to claim 1, wherein the cranberry-derived proanthocyanidin extract is obtained from a flower, root, leaf, stem and/or fruit of the *Vaccinium macrocarpon*.

9. The method according to claim 1, wherein the nosocomial respiratory infection is in the trachea.

10. The method according to claim 2, wherein the nosocomial respiratory infection is in the trachea.

11. The method according to claim 3, wherein the nosocomial respiratory infection is in the trachea.

* * * * *